(12) United States Patent
Crooks et al.

(10) Patent No.: US 9,810,658 B2
(45) Date of Patent: Nov. 7, 2017

(54) METHOD FOR THE DETECTION AND QUANTIFICATION OF ANALYTES USING THREE-DIMENSIONAL PAPER-BASED DEVICES

(71) Applicant: Board of Regents, The University of Texas System, Austin, TX (US)

(72) Inventors: Richard M. Crooks, College Station, TX (US); Hong Liu, Nanjing (CN); Karen Scida, Austin, TX (US); Christophe Renault, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1192 days.

(21) Appl. No.: 13/865,352

(22) Filed: Apr. 18, 2013

(65) Prior Publication Data

US 2015/0355132 A1 Dec. 10, 2015

Related U.S. Application Data

(60) Provisional application No. 61/635,081, filed on Apr. 18, 2012, provisional application No. 61/641,880, (Continued)

(51) Int. Cl.
*B01L 3/00* (2006.01)
*G01N 27/327* (2006.01)
(Continued)

(52) U.S. Cl.
CPC ........ *G01N 27/3276* (2013.01); *B01L 3/5023* (2013.01); *B01L 3/50273* (2013.01); *B01L 3/502707* (2013.01); *B01L 3/502715* (2013.01); *B01L 3/502738* (2013.01); *C12Q 1/001* (2013.01); *C12Q 1/6813* (2013.01); *G01N 33/5438* (2013.01); *G01N 33/54373* (2013.01);
(Continued)

(58) Field of Classification Search
None
See application file for complete search history.

(56) References Cited

U.S. PATENT DOCUMENTS

2007/0000776 A1 1/2007 Karube et al.
2008/0019866 A1 1/2008 Paek et al.
(Continued)

FOREIGN PATENT DOCUMENTS

KR 20110028019 3/2011

OTHER PUBLICATIONS

Liu et al., Three-Dimensional Paper Microfluidic Devices Assembled Using the Principles of Origami, Journal of the American Chemical Society, 133 (44), pp. 17564-17566, published online Oct. 17, 2011.*
(Continued)

*Primary Examiner* — Rebecca Martinez
(74) *Attorney, Agent, or Firm* — Meunier Carlin & Curfman LLC

(57) ABSTRACT

Described herein are three-dimensional (3-D) paper fluidic devices. The entire 3-D device is fabricated on a support layer formed from a single sheet of material and assembled by folding the support layer. The folded structure may be enclosed in an impermeable cover or package. Chemically sensitive particles may be disposed in the support layer for use in detecting analytes.

19 Claims, 16 Drawing Sheets

Related U.S. Application Data filed on May 2, 2012, provisional application No. 61/756,772, filed on Jan. 25, 2013.

(51) Int. Cl.

| | |
|---|---|
| *G01N 33/543* | (2006.01) |
| *C12Q 1/00* | (2006.01) |
| *C12Q 1/68* | (2006.01) |
| *G01N 35/00* | (2006.01) |
| *G01N 33/487* | (2006.01) |

(52) U.S. Cl.
CPC ......... *B01L 3/5055* (2013.01); *B01L 2200/12* (2013.01); *B01L 2300/045* (2013.01); *B01L 2300/0627* (2013.01); *B01L 2300/0645* (2013.01); *B01L 2300/0816* (2013.01); *B01L 2300/0877* (2013.01); *B01L 2300/126* (2013.01); *B01L 2400/0406* (2013.01); *B01L 2400/065* (2013.01); *G01N 33/48707* (2013.01); *G01N 2035/00158* (2013.01); *Y10T 29/49984* (2015.01)

(56) References Cited

U.S. PATENT DOCUMENTS

2011/0111517 A1* 5/2011 Siegel .............. B01L 3/502707
436/164
2011/0123398 A1 5/2011 Carrilho et al.

OTHER PUBLICATIONS

Govindarajan et al., A low cost point-of-care viscous sample preparation device for molecular diagnosis in the developing world; an example of microfluidic origami, Lab Chip, 12, pp. 174-181, published on Nov. 8, 2011.*

Fenton et al. "Multiplex Lateral-Flow Test Strips Fabricated by Two-Dimensional Shaping" ACS Appl. Mater. Interfaces, 2009, 1 (1), 124-129.

Unger et al. "Monolithic Microfabricated Valves and Pumps by Multilayer Soft Lithography" Science 2000 288:113.

Schilling et al. "Fully Enclosed Microfluidic Paper-Based Analytical Devices" Anal. Chem., 2012, 84 (3), pp. 1579-1585.

Kartalov et al. "Microfluidic vias enable nested bioarrays and autoregulatory devices in Newtonian fluids" PNAS (2006) 103:33, 12280-12284.

Martinez et al. "Three-dimensional microfluidic devices fabricated in layered paper and tape" PNAS (2008) 105:50, 19606-19611.

Martinez et al. "Patterned Paper as a Platform for Inexpensive, Low Volume, Portable Bioassays" Angew Chem Int Ed Engl. 2007 ; 46(8): 1318-1320.

Marinez et al. "FLASH: A rapid method for prototyping paper-based microfluidic devices" Lab Chip. Dec. 2008 ; 8(12): 2146-2150.

Cheng et al. "Paper-Based ELISA" Angew Chem Int Ed Engl. 49:28, pp. 4771-4774, 2010.

International Preliminary Report on Patentability for PCT Application No. PCT/US2013/037082 issued Oct. 21, 2014.

Dungchai et al. "Electrochemical Detection for Paper-Based Microfluidics" Anal. Chem. 2009, 81, 5821-5826.

Lu et al. "Rapid prototyping of paper-based microfluidics with wax for low-cost, portable bioassay" Electrophoresis (2009) 30: 1497-1500.

Osborn et al. "Microfluidics without pumps: reinventing the T-sensor and H-filter in paper networks" Lab Chip, 2010, 10, 2659-2665.

Nie et al. "Integration of paper-based microfluidic devices with commercial electrochemical readers" Lab Chip. Nov. 21, 2010; 10(22): 3163-3169.

Martinez et al. "Diagnostics for the Developing World: Microfluidic Paper-Based Analytical Devices" Anal. Chem. 2010, 82, 3-10.

Martinez et al. "Programmable diagnostic devices made from paper and tape" Lab Chip, 2010, 10, 2499-2504.

Siegel et al. "Foldable Printed Circuit Boards on Paper Substrates" Adv. Funct. Mater. 2010, 20, 28-35.

Xiang et al. "Using personal glucose meters and functional DNA sensors to quantify a variety of analytical targets" Nature Chemistry 3, 697-703.

Carrilho et al. "Understanding Wax Printing: A Simple Micropatterning Process for Paper-Based Microfluidics" Anal. Chem. 2009, 81, 7091-7095.

International Search Report/Written Opinion for PCT Application No. PCT/US2013/037082 issued Aug. 12, 2013.

* cited by examiner

Antibody Present         Antibody Not Present

Mix 2° Ab/Gox with sample

Mix with supported Antigen

Separate beads from liquids

No GOx

= 2° Antibody / Glucose Oxidase ("2°Ab/GOx")      = 1° Antibody ("1°AB")

= Particle with support Antigen

SEQUENCE LISTING

<160> NUMBER OF SEQ ID NOS: 5

<210> SEQ ID NO 1
<211> LENGTH: 12
<212> TYPE: DNA
<213> ORGANISM: Artificial Sequence
<220> FEATURE:
<223> OTHER INFORMATION: Synthetic sequence

<400> SEQUENCE: 1
tgagtagaca ct                                                           12

<210> SEQ ID NO 2
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 2
tctcttggac cc                                                           12

<210> SEQ ID NO 3
<211> LENGTH: 44
<212> TYPE: DNA
<213> ORGANISM: Artificial Sequence
<220> FEATURE:
<223> OTHER INFORMATION: Synthetic Sequence

<400> SEQUENCE: 3
actcatctgt gaagagaacc tgggggagta ttgcggagga aggt                         44

<210> SEQ ID NO 4
<211> LENGTH: 48
<212> TYPE: DNA
<213> ORGANISM: Artificial Sequence
<220> FEATURE:
<223> OTHER INFORMATION: Synthetic Sequence

<400> SEQUENCE: 4
aaaaaaaaaa aatgagtaga cacttctctt ggacccaaaa aaaaaaaa                     48

<210> SEQ ID NO 5
<211> LENGTH: 50
<212> TYPE: DNA
<213> ORGANISM: Artificial Sequence
<220> FEATURE:
<223> OTHER INFORMATION: Synthetic Sequence

<400> SEQUENCE: 5 tttttactc atctgtgaag agaacctggg ggagtattgc ggaggaaggt                    50

METHOD FOR THE DETECTION AND QUANTIFICATION OF ANALYTES USING THREE-DIMENSIONAL PAPER-BASED DEVICES

PRIORITY CLAIM

This application claims priority to U.S. Provisional Application Ser. No. 61/635,081 entitled "3-D FLUIDIC ANALYTICAL DEVICE FABRICATED BY PAPER FOLDING" filed Apr. 18, 2012; U.S. Provisional Application Ser. No. 61/641,880 entitled "3-D SENSING SYSTEMS FABRICATED BY PAPER FOLDING" filed May 2, 2012; and U.S. Provisional Application Ser. No. 61/756,772 entitled "METHOD FOR THE DETECTION AND QUANTIFICATION OF ANTIBODIES" filed Jan. 25, 2013, which are incorporated herein by reference in its entirety.

STATEMENT REGARDING FEDERALLY SPONSORED RESEARCH OR DEVELOPMENT

This invention was made with government support under HR0011-12-2-0003 awarded by Defense Advanced Research Projects Agency, and support under W911NF-07-1-0330 awarded by the U.S. Army Research Office and the U.S. Defense Threat Reduction Agency. The government has certain rights in the invention.

BACKGROUND OF THE INVENTION

1. Field of the Invention

The invention generally relates to fluidic devices for chemical analysis.

2. Description of the Relevant Art

The principles of two-dimensional (2-D) and three-dimensional (3-D) microfluidic paper analytical devices (μPADs) have been described by various research groups and a number of interesting applications have been reported. Briefly, for 2-D μPADs, microfluidic channels and reservoirs are fabricated by patterning channel walls on chromatography paper using a liquid-impermeable material, such as photoresist (PR) or wax. Aqueous solutions are then driven along the hydrophilic paper channels by capillary action. For 3-D μPADs, individual layers are patterned sequentially by photolithography and then stacked using double-sided tape. Holes are punched in the tape using a laser cutter, and the resulting holes are filled with cellulose powders or are compressed to provide vertical connections between adjacent layers. The results of an analysis are determined using colorimetric detection on one of the two surface layers.

The 3-D μPADs show great promise for applications such as power-free, point-of-care detection and diagnosis, particularly in underdeveloped or remote areas. However, as presently practiced, 3-D device fabrication requires a photolithographic step for each layer and then laser cutting of vias to establish fluidic connections between layers. Moreover, assembly of the device using double-sided tape is irreversible so that only the surface layer can be used for colorimetric detection. The approach we describe addresses these points.

SUMMARY OF THE INVENTION

Described herein is a fluidic analytical device that includes: a support layer, wherein the support layer comprises a single sheet of material capable of transporting a liquid using capillary action; and a plurality of channel walls formed on the support layer, wherein the channel walls define channels on the support layer, wherein a fluid added to the support layer in one or more of the channels is conducted through the channels by capillary action. In an embodiment, the support layer comprises paper. The channel walls are formed from a liquid impermeable material. For example the channel walls may be formed from a photoresist material or a solid wax material.

The channel walls may define one or more inlets, one or more reservoirs, and one or more channels that direct a fluid from the inlet to the reservoir. In some embodiments, the reservoir includes a reagent for chemical analysis. The reagent may be a reagent for electrochemical analysis. A chemically sensitive material, herein also referring to biochemical materials, in some embodiments, is disposed in the support layer in one or more of the channels, wherein the chemically sensitive material is capable of producing a detectable signal when an analyte is present. The chemically sensitive material may be antibody sensitive particles capable of binding to antibodies in a fluid sample.

In some embodiments, the fluidic analytical device comprises a first channel and a second channel, wherein the first channel comprises chemically sensitive particles, and wherein the second channel comprises chemically inert particles. Electrodes may be formed on the support layer using a conductive material. Electrodes may be used to monitor electrochemical reactions in the support layer. The support layer may be encapsulated in a polymeric material.

The fluidic device may include a removable strip coupled to the support layer, wherein fluid passes through one or more channels of the support layer onto the removable strip during use. The removable strip may be positionable within the support to alter the flow of fluids through one or more channels. The fluidic device may include liquid conductive zones that connect one or more layers, inlets, reservoirs, channels coupling the inlets to the reservoirs, vias that couple layers to each other, and water-impermeable barriers that redirect the fluid path into an adjacent conductive zone.

In some embodiments, the support layer comprises a top layer comprising a plurality of reservoirs and a bottom layer comprising a plurality of reservoirs, wherein the plurality of reservoirs in the top layer are alignable with the plurality of reservoirs of the bottom layer by sliding the top layer over the bottom layer.

In an embodiment, a method of detecting an analyte includes obtaining a fluidic analytical device. The fluidic analytical device includes a support layer, wherein the support layer comprises a single sheet of material capable of transporting a liquid using capillary action; a plurality of channel walls formed on the support layer, wherein the channel walls define channels on the support layer, wherein a fluid added to the support layer in one or more of the channels is conducted through the channels by capillary action; and chemically sensitive material disposed in the support layer in one or more of the channels, wherein the chemically sensitive material is capable of producing a detectable signal when the an analyte is present. The method includes adding a fluid containing the analyte to one or more of the channels and observing a change in the properties of the analytical device, wherein a change in the properties of the analytical device indicate the presence of an analyte. The change in the properties of the analytical device may be a change in an optical property of the analytical device.

In some embodiments, the change in optical property is observed in one or more of the channels that include the chemically sensitive material. In some embodiments the first channel and the second channel contain a detection zone, and the change in property is determined by measuring an electrochemical or electrical signal in the detection zone. In some embodiments, the first channel comprises chemically sensitive particles, and wherein the second channel comprises chemically inert particles. The change in the properties of the analytical device may be determined by comparing a change of the optical property of the first channel with respect to the second channel.

In some embodiments, the first channel and the second channel feed into a reservoir. The change in property may be determined by measuring an electrical or electrochemical feature of the reservoir. The electrical or electrochemical feature of the reservoir is measured using a voltmeter, ammeter, or potentiostat. The electrical or electrochemical feature may be amplified using a capacitor or other suitable amplification device.

In one embodiment, a method of forming a fluidic device includes: forming a plurality of channel walls on a support layer, wherein the support layer is a single sheet of material capable of transporting a liquid using capillary action; and folding the support layer to align one or more of the formed channel walls such that one or more channels are defined on the support layer. Once the channels have been defined, chemically sensitive molecules or particles are applied to the support layer such that the chemically sensitive molecules or particles are disposed in the support layer in one or more of the channels. The channel walls may be formed using photolithography. One or more of the channel walls may define one or more inlets and one or more reservoirs. In one embodiment, folding the support layer creates a three dimensional fluidic device that includes inlets, reservoirs and channels coupling the inlets to the reservoirs. The inlets and reservoirs may be at different levels of the fluidic device.

In one embodiment, a method of detecting an antibody in a sample includes preparing a mixture of the sample with a secondary antibody, raised against a second epitope on the primary antibody, and that is coupled to an enzyme and a supported antigen, wherein the antibody in the sample binds to the supported antigen and the secondary antibody; separating a liquid from the supported antigen in the mixture, wherein the separated liquid comprises unreacted secondary antibody that is coupled to an enzyme; reacting the separated liquid with a known amount of an enzymatic substrate for the enzyme coupled to the secondary antibody; and determining the change in product concentration after the enzymatic substrate is reacted with the separated liquid, wherein the concentration of antibody in the sample is proportional to the change in the amount of enzymatic product. In one embodiment, preparing a mixture of the sample with a secondary antibody that is coupled to an enzyme and a supported antigen includes: preparing a composition of the secondary antibody that is coupled to an enzyme with the sample; and adding the supported antigen to the composition to form the mixture of the sample with a secondary antibody that is coupled to an enzyme and a supported antigen. In an alternate embodiment, preparing a mixture of the sample with a secondary antibody that is coupled to an enzyme and a supported antigen includes: preparing a composition of the supported antigen with the sample; and adding the secondary antibody that is coupled to an enzyme to the composition to form the mixture of the sample with a secondary antibody that is coupled to an enzyme and a supported antigen. The supported antigen may be an antigen coupled to a polymeric bead.

In an embodiment, the method may be performed using a fluidic analytical device. The fluidic analytical device may include a support layer, wherein the support layer includes a single sheet of material capable of transporting a liquid using capillary action; a plurality of channel walls formed on the support layer, wherein the channel walls define channels on the support layer, wherein a fluid added to the support layer in one or more of the channels is conducted through the channels by capillary action; and supported antigen disposed in the support layer in one or more of the channels, and a receiving reservoir coupled to the one or more channels. The method includes collecting the separated liquid in the receiving reservoir. In an embodiment, the fluidic analytical device comprises a first channel and a second channel, wherein the first channel comprises supported antigen particles, and wherein the second channel comprises chemically inert particles. The first channel and the second channel may feed into a reservoir that includes a known amount of the enzyme substrate. Determining the change in enzyme substrate concentration is performed by measuring an electrical or electrochemical feature of the reservoir.

In one embodiment a chemically sensitive particle may be designed to capture one or more antibodies of interest. For example, a chemically sensitive particle may include one or more antigens that evoke the production of one or more antibodies of interest. The antigens may be coupled to a polymeric support (e.g., a bead). During use, when a sample is introduced to the chemically sensitive particles, antibodies to the supported antigens are captured by the chemically sensitive particle. While any antigen-antibody combination may be used in a detection system, of particular interest are detection systems for polio, measles, hepatitis A, hepatitis B, tetanus, cholera, yellow fever, typhoid, diphtheria, tuberculosis, plague, rabies, influenza, and dengue virus.

In one embodiment, the concentration of antibodies in a subject may be determined by converting an antibody reaction with a chemical agent into a glucose signal which correlates to the concentration of antibody. The glucose signal may be read using a potentiometer (as discussed above) or preparing a test strip which can be read in a personal glucose meter. A "glucose signal" means a measureable amount or concentration of glucose.

In one embodiment, the concentration of antibodies in a subject may be determined by coupling an antibody reaction with catalytic metal nanoparticles for amplification to generate a chemical or electrochemical signal which correlates to the concentration of antibody. A "chemical signal" means a measureable amount or concentration of a specified chemical. An "electrochemical signal" means a voltage or current measured using an electrode.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
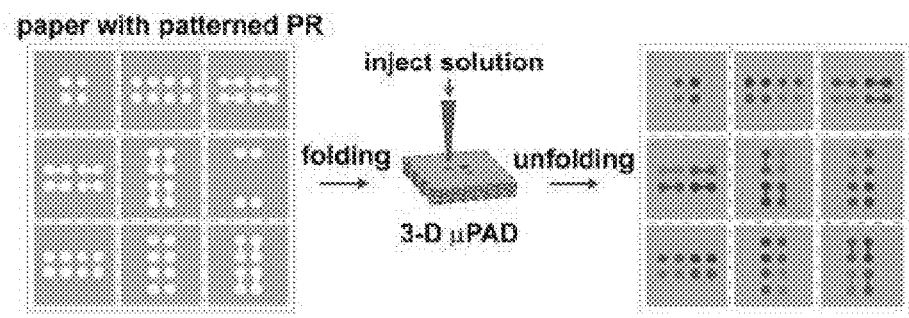
FIG. 1 depicts a schematic diagram of the formation and use of a fluidic analytical device assembled using the principles of origami.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Described herein is a method for fabricating three-dimensional (3-D) fluidic devices that is based on the principles of origami (paper folding). The concept is illustrated in FIG. 1. Using this method, a portion of, or even the entire device may be fabricated on a single sheet of a flat material, and then assembled by paper folding. This method offers several advantages over previous methods. First, instead of sequential layer-by-layer fabrication, which is the usual approach for preparing 3-D fluidic systems, the device may be fabricated on a single substrate in a single photolithographic step. This speeds the fabrication process and reduces cost. Second, the multilayer device may be assembled by folding, which can be completed rapidly, in less than 1 min, optionally by hand, without tools or special alignment techniques. Third, the device can be easily unfolded so that all layers, rather than just the surface, can be used for parallel analysis. Fourth, incorporation of additional intermediate layers should not result in much additional fabrication overhead.

Origami is the traditional Japanese art of paper folding, and it has been in use for about 400 years to construct 3-D geometries starting with a single piece of flat paper. Within the context of modern science and engineering, there has not been much interest in origami. We show here that origami can be used to fabricate elegant and functional fluidic devices, which we call origami paper analytical devices (oPADs), having several highly desirable characteristics. In one embodiment, an analytical device may be formed by forming a plurality of channels on a support layer. The support layer may include a single sheet of material capable of transporting a liquid using capillary action. Materials that may be used include papers, such as chromatography paper, and other fibrous materials. The channels are defined by a plurality of channel walls formed on the support, which create barriers within the capillary material that direct the flow of liquid through the support. The channels form a fluid path for liquids from an inlet to a reservoir where the content of the liquid can be analyzed. The channels may be patterned such that, upon folding the support in a predetermined manner, the fluid is directed along a path from an inlet to a reservoir, and along the way the fluid may interact with chemically or biochemically sensitive materials. The rate of fluid transport through the device may be controlled, for example by the size of the channels (width and thickness), the shape of the channels, the porosity of the capillary material, the surface properties of the capillary material, and the availability of a reservoir into which the fluid may flow. The folded analytical device can be placed in a holder to protect it or to provide additional functionality such as holding the individual layers together in close proximity.

FIG. 2A shows a piece of chromatography paper that has been patterned with channels, reservoirs, and a frame (to provide a template for subsequent folding) fabricated in a single photolithographic step. The entire photolithographic process can be performed without a cleanroom, using just a hot plate, UV lamp, and a mask produced on a printer. The patterning of photoresist (e.g., SU-8 photoresist) on chromatography paper was performed by soaking the chromatography paper in the photoresist for 5 min. After soft baking at 130° C. for 10 min on a hot plate and cooling to room temperature, the paper was exposed to UV light (365 nm, 350 W lamp) for 30 s under a transparency mask. Next, the paper was post baked at 130° C. for 10 min on a hotplate. Finally, the paper was immersed in acetone for 1 min to remove the unexposed photoresist. All channels patterned on the paper were 900 μm wide, and the reservoirs were 2.5 mm in diameter. Individual layers of the paper device were 2 cm by 2 cm.

Photoresist, as used herein, refers to any material in which the solubility of the material may be altered by the application of activating light (e.g., UV light). Either positive photoresist materials or negative photoresist materials may be used to from the channels. A positive photoresist a type of photoresist in which the portion of the photoresist that is exposed to light becomes soluble to the photoresist developer. The portion of the photoresist that is unexposed remains insoluble to the photoresist developer. A negative photoresist is a type of photoresist in which the portion of the photoresist that is exposed to light becomes insoluble to the photoresist developer. The unexposed portion of the photoresist is dissolved by the photoresist developer. Materials that may be used as negative photoresists include bis-epoxides (e.g., SU-8) and bisazides.

The paper can also be patterned using wax printing. Wax printed channels are particularly useful for water based analytical systems, as the water-insoluble wax channels direct the liquid through the paper. An inkjet printer may be used to print wax material. For example, a wax-based solid ink may be used. Many types of wax-based solid ink are commercially available and are particularly useful for forming channels as the ink provides a visual indication of the location of the channels. However, it should be understood, that the wax material used to form the channels does not require an ink to be functional. Examples of wax materials that maybe used include polyethylene waxes, hydrocarbon amide waxes or ester waxes. The paper was then placed on a hot plate with the wax side up for 15 s at 120° C., and then cooled to room temperature.

Following patterning of the paper and loading of reagents on the paper, the 3-D device was assembled by folding the paper along the lithographically defined frame. The frame ensures that the channels and reservoirs are properly aligned after folding into the 3-D assembly. Paper folding was carried out using the sequence illustrated in FIG. 3. The numbers at the upper-left corner of each layer indicate the sequential ordering of the folded device. The four corners of the folded paper were trimmed, as shown in parts FIG. 2B and FIG. 2C, to accommodate an aluminum clamp or holder (FIG. 2D). Solutions could then be injected into the four holes drilled into the top aluminum plate of the clamp or holder (FIG. 2D) so that solutions could be injected into the device.

Importantly, this origami assembly method does not require adhesive tape, which can lead to contamination and nonspecific adsorption. Avoiding tape also speeds the assembly of the device and eliminates the need for laser cutting. The photoresist pattern serves as the channel wall to separate solutions into different channels in all three dimensions. As described previously, the vertical connections (or "vias") are made by direct contact of paper channels or reservoirs on adjacent layers, and this avoids the use of cellulose powders to provide a fluidic connection between layers. The vertical connections are achieved spontaneously by paper folding, and the folded paper is sandwiched (or otherwise held or constrained, for example by lamination) between two flat substrates to ensure robust fluid connection between channels on adjacent layers and effective barrier to flow between channel walls on adjacent layers. Once the paper is folded, no manual operation is required to enable the vertical connections. Vias can control access between layers. For example, a water-impermeable barrier may span a channel on a first layer, preventing passage of liquid directly down the channel, while an adjacent second layer overlaps the channel in the first layer, forming a via, and providing a second layer conduction zone, which may contain active components. The second layer conduction zone may overlap both sides of the impermeable cross-channel barrier in the first layer, in which case fluid is directed vertically into the second layer conduction zone, operated upon therein, then redirected back down to the first layer on the opposite side of the cross-channel barrier. The cross-sectional area of the vias may be used to control the rate of fluid flow between layers.

oPADs may be as simple as a paper analytical device with a single fold to create two adjacent paper layers. oPADs can also be contemplated that are more complicated folded paper structures, including three-dimensional shapes, or reconfigurable folded structures, such as flexagons. Flexagons can be flexed or folded in certain ways to reveal internal faces in addition to the two original back and front faces. For example, by flexing a hexahexaflexagon, six distinct flat hexagonal faces can be revealed, cup-shaped structures can be made, and different layers of paper can be brought adjacent to and in contact with other faces. In an embodiment of the invention, a paper analytical device comprises a flexagon. In a further embodiment, a layer of a paper analytical device is a face of a flexagon, and said face is brought adjacent to and in contact with another layer by flexing the flexagon. This is useful for washing steps, adding reagents, mixing, timing, and various other operations that would be apparent to one skilled in the art.

In another embodiment, the folded paper device may be enclosed in a package to inhibit contamination, fluidic evaporation and problems that may arise due to direct exposure of the device to air. In this embodiment, the folded paper device, which may be preloaded with reagents (i.e., chemically sensitive materials), is sandwiched and enclosed in a polymeric package. The polymeric package may be formed by a lamination process in which the folded paper device is placed between two layers of the polymeric material and the layers are joined together to form a sealed device. Joining of the polymeric material may be accomplished by use of a heat process in which the materials are heated past a glass transition temperature of the materials or by the use of pressure sensitive adhesives. These processes cause the materials to adhere to each other when the heat is removed, creating a sealed polymeric package. In a preferred embodiment, only the edges of the polymeric materials are sealed to create a package that is edge-sealed. This process protects the paper fluidic device, and any reagents predisposed in the device, from becoming damaged by the heat/pressure process. When heat-sensitive reagents are not part of the device, the entire device can be heated in order to seal the package. A metal-foil-backed polymer laminate film may be used to decrease evaporation further. In one embodiment, sealing elements (for example, photoresist or wax strips) may be printed on one or more layers in such a way as to align on the edges of the device after folding. This allows the sealing elements to be re-melted and create a continuous barrier connecting the layers and sealing the device, for example around its perimeter or around internal features.

Various types of equipment may be used to create a package for a fluidic device. In one embodiment, a pouch laminator may be used. A pouch laminator uses a lamination pouch that is coated with a heat-activated film or pressure sensitive film that seals the pouch. In an embodiment, the paper fluidic device is placed in a pouch having a sealing edge. The sealing edge includes the heat activated adhesive. The sealing edge is positioned in an edge heat sealer, where it is heated to seal the paper fluidic device in the pouch. This method avoids heating of the paper fluidic device during the packaging step. Alternatively, a pressure sensitive adhesive may be present on the sealing edge of the pouch. The sealing edge may be placed in a press that creates pressure on the edge, causing the edge to become sealed.

In other embodiments, a heated roll laminator may be used to package the paper fluidic device. The heated roll laminator uses heated rollers to melt glue extruded onto a lamination film. This lamination film comprising hot glue is then applied to the paper fluidic device using pressure rollers. Upon cooling the paper fluidic device is sealed with the lamination film.

Cold roll laminators may also be used to create a package for the fluidic device. Cold roll laminators use a plastic film which is coated with an adhesive and glossy backing which does not adhere to the glue. When the glossy backing is removed, the adhesive is exposed, which then sticks directly onto the item which needs to be laminated. This method is suitable for paper fluidic devices that would be damaged by heat.

Packaged fluidic devices are resistant to fluidic evaporation. For example, packaged fluidic devices have been tested at 37° C. for two hours, with no or minimal evaporation of fluid. Resistance to evaporation allows the packaged paper fluidic device to be used at temperatures above room temperature that favor chemical or bioassays. For example, many chemical or bioassays are accelerated at temperature of about 37° C. Paper devices that are not packaged tend to lose fluid through evaporation, making testing above room temperature difficult. The resistance to evaporation may be important for immunoassays and DNA assays that require incubation at 37° C. for extended periods of time. Packaging using a polymeric laminate structure also allows connections between fluidic channels on adjacent layers, creating a 3-D fluidic network. Due to enclosing of the paper fluidic device, the deformation of the fluidic devices due to swelling of paper is also inhibited.

One can fabricate electrodes or wires on the paper analytical device, for example by screen printing conductive ink such as carbon ink onto a support layer. These may be positioned in such a way as to provide functions to the device once it is assembled, including for example: integrated electronic components, electrical capacitors, batteries, electrodes for an electrochemical cell, heating using electrical resistance, for example for the purpose of making or breaking seals, drying, dissolving, generating bubbles. Bubbles generated by integrated electrodes or wires can be used to move materials in the device, block channels or electrodes, and other purpose that will be apparent to those skilled in the art.

Figure 2:
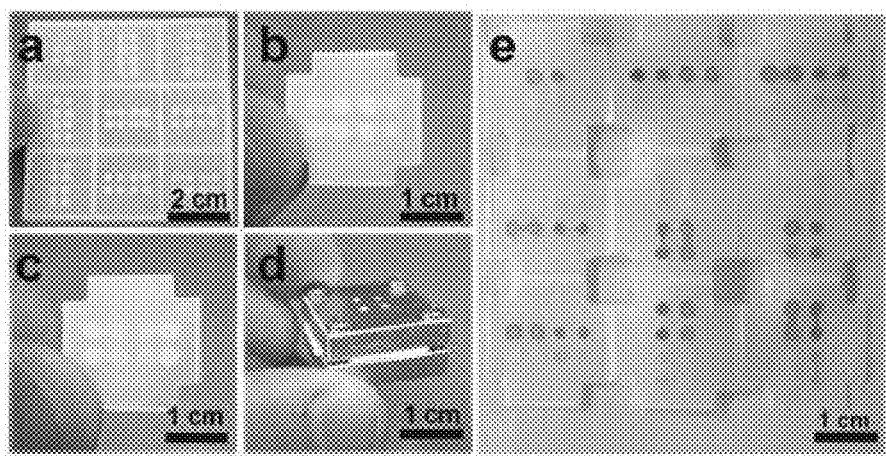
FIGS. 2A-E depict an embodiment of a fluidic analytical device and the use of the device.
Figure 3:
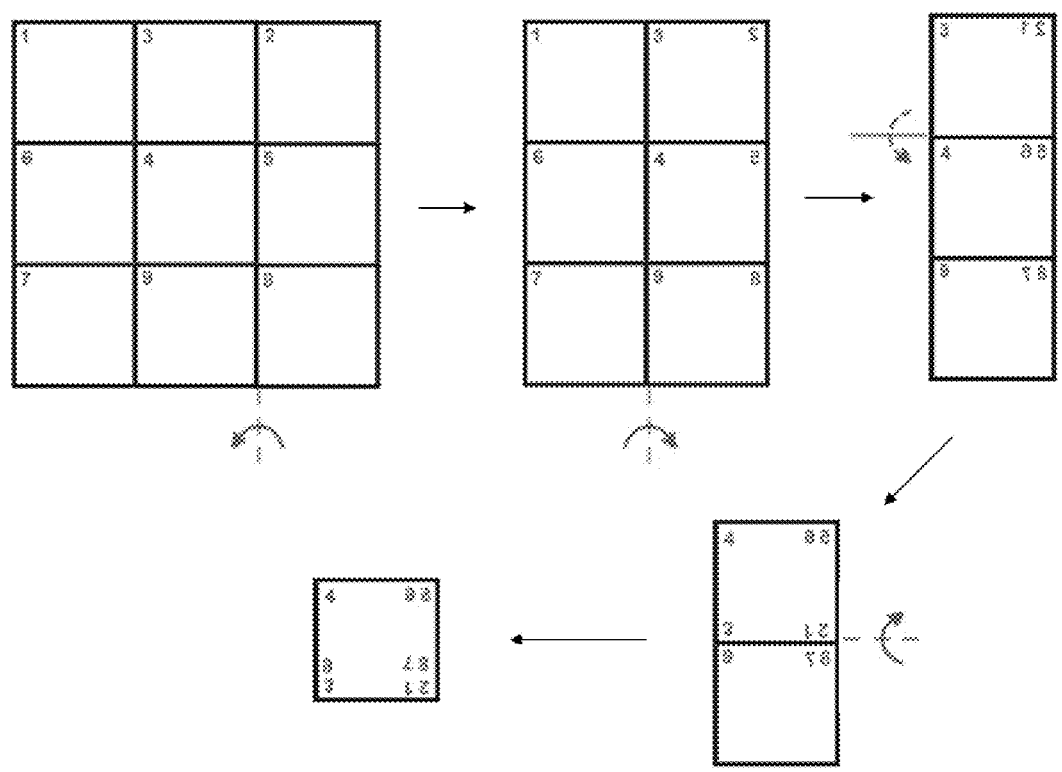
FIG. 3 depicts a paper folding sequence used to assemble the device of FIGS. 2A-E.

The nine-layer device shown in FIG. 2 was used to demonstrate the ability of the origami device to direct the flow of fluids in three dimensions. Specifically, 10.0 μL of the following four 1.0 mM aqueous solutions were injected through the openings in the top plate of the clamp: rhodamine 6G (red), erioglaucine (blue), tatrazine (yellow), and erioglaucine mixed with tatrazine (1:10, green). After 5 min, the device was unfolded, and, as shown in FIG. 2E, the solutions flowed through their designated channels and reservoirs without mixing.

Figure 4:
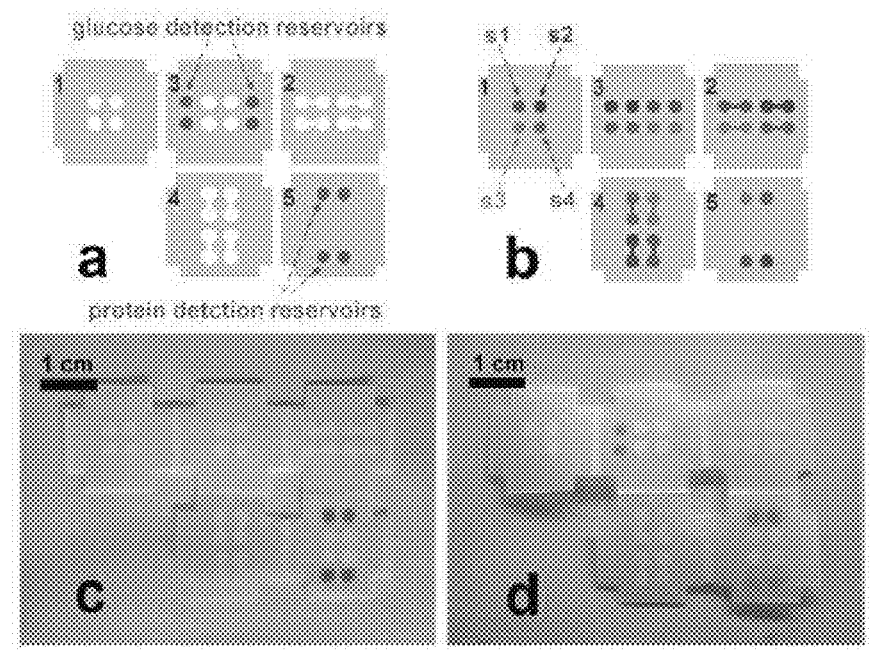
FIGS. 4A-D depict the test results of glucose and BSA determination using a fluidic analytical device.

As mentioned earlier, every layer of the device can be used for parallel chemical analysis of multiple analytes. This is because the paper can be unfolded after analysis to reveal a permanent record of the assay. This aspect of the method might be useful for multiplexed detection and high-throughput screening. To demonstrate this principle, a two-analyte colorimetric assay of glucose and protein (bovine serum albumin, BSA) was carried out using a single 3-D oPAD device comprising five layers and assembled by origami, depicted in FIG. 4. The following chemical reactions were used to detect glucose and the protein:

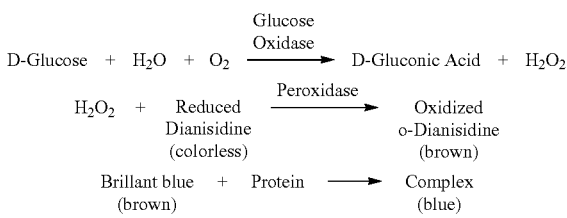

The experiment was performed as follows. First, the detection reservoirs (FIG. 4A) were preloaded with commercially available reagents for the colorimetric detection of glucose and BSA. The device, including the reagents, was dried at 20° C. for 30 min. Second, four 5.0 μL aliquots containing different amounts of glucose and BSA were injected into the four inlets at the top of the device (FIG. 4B). The samples flowed toward the detection reservoirs, and a portion of these samples were allowed to react with the preloaded reagents for 10 min. Finally, the paper was unfolded so that both layers having detection reservoirs were accessible for colorimetric analysis. The degree of color change is directly related to the concentration of glucose or protein in the samples.

A comparison of FIG. 4C and FIG. 4D indicates that the assay was successful and that there was no mixing between channels or reservoirs. Specifically, the color of the solution in the detection reservoirs exposed to glucose (samples s2 and s4, FIG. 4B) or BSA (samples s3 and s4) changed from colorless to brown or from brown to blue, respectively. Although only two layers on the device were required for this very simple colorimetric assay, it is obvious that more complex analysis could be performed. To scale up the device for analyzing more analytes or more samples, additional layers might be required. However, since all layers of the multilayer network are fabricated simultaneously, the addition of more layers or more complex structures does not present much of a practical barrier.

Fluorescence detection usually provides substantially higher sensitivity and lower detection limits than simple colorimetric measurements. However, to the best of our knowledge, fluorescence detection has not thus far been used for 3-D μPAD-based assays. Accordingly, we fabricated three-layer oPADs (similar to the device illustrated in FIG. 4B, but with just three layers) that could be used to carry out four simultaneous BSA assays using fluorescence detection. The assay is based on the dye epicocconone, which exhibits enhanced fluorescence in the presence of BSA. The assay for BSA using the paper device was carried out as follows. First, 1.0 μL of a buffered epicocconone solution was spotted onto each detection reservoir and then dried at 20° C. for 5 min. Second, 3.0 μL aliquots of buffered BSA solutions were injected into the four inlets at the top of the device. Third, the oPAD was placed in a humidity chamber for 30 min, during which time the BSA solutions passed to the detection reservoirs and reacted with the preloaded fluorescent dye. Finally, the bottom layer of the device was scanned using a fluorescence imager. Each scan was performed at 100 μm resolution and was complete within 1 min.

Figure 5:
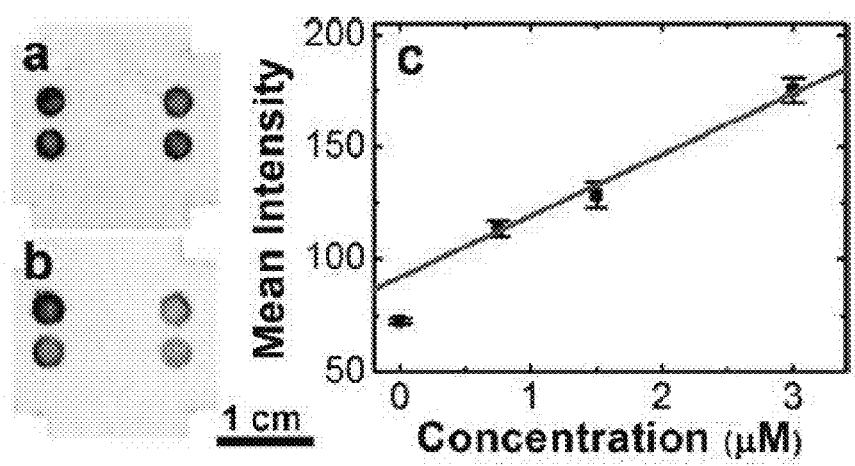
FIGS. 5A-C depict test results of a method of quantifying BSA by fluorescence using a fluidic analytical device.

FIG. 5A shows the result of an assay in which all four BSA aliquots were of the same concentration (3.0 μM), while in FIG. 5B the concentrations of BSA were different (0, 0.75, 1.50, and 3.00 µM). Qualitatively, FIG. 5B shows that the color of the detection reservoirs becomes darker as the concentration of BSA increases. To quantify these results, the images were imported into Adobe Photoshop CS2 and transferred to gray-scale mode. The mean fluorescence intensity was determined from the image histogram for each detection reservoir, and then it was background-corrected by subtracting the average intensity measured at the center of the paper where no BSA was present. These data constitute a calibration curve, which is shown in FIG. 5C. The error bars represent the standard deviation of at least three independent measurements. The detection limit, defined as 3 times the standard deviation of the sample containing no BSA (0 µM) divided by the slope of the calibration curve, is 0.14 µM BSA. Because the fluorescence intensity, rather than the color change, is directly proportional to protein concentration, quantification by fluorescence is more straightforward than colorimetric detection.

In some embodiments, a chemically sensitive material (e.g., particles such as beads with bound receptor molecules) may be embedded in the channels and/or reservoirs of the paper fluidic device to allow various chemical testing for analytes of interest. A chemically or biochemically sensitive material, in some embodiments, possesses both the ability to bind the analyte of interest and to create a modulated signal. The material may include receptor molecules which posses the ability to bind the analyte of interest and to create a modulated signal. Alternatively, the material may include receptor molecules and indicators. The receptor molecule may posses the ability to bind to an analyte of interest. Upon binding the analyte of interest, the receptor molecule may cause the indicator molecule to produce the modulated signal. The receptor molecules may be naturally occurring or synthetic receptors formed by rational design or combinatorial methods. Some examples of natural receptors include, but are not limited to, DNA, RNA, aptamers, proteins, enzymes, oligopeptides, antigens, antibodies, biological cells, bacteria, viruses, and boronate ligands that bind glycated proteins such as glycated hemoglobin. Either natural or synthetic receptors may be chosen for their ability to bind to the analyte molecules in a specific manner. The forces which drive association/recognition between molecules include the hydrophobic effect, electrostatic attraction, van der Waals interaction, and hydrogen bonding. The relative strengths of these forces depend upon factors such as the solvent dielectric properties, the shape of the host molecule, and how it complements the guest. Upon host-guest association, attractive interactions occur and the molecules stick together. The most widely used analogy for this chemical interaction is that of a "lock and key". The fit of the key molecule (the guest) into the lock (the host) is a molecular recognition event.

A naturally occurring or synthetic receptor molecule may be bound to a polymeric resin in order to create a chemically sensitive particle. The polymeric resin may be made from a variety of polymers including, but not limited to, agarose, dextrose, acrylamide, controlled pore glass beads, styrene polymers, styrene copolymers, polystyrene-polyethylene glycol resin, polystyrene-divinyl benzene resin, formylpolystyrene resin, trityl-polystyrene resin, acetyl polystyrene resin, chloroacetyl polystyrene resin, aminomethyl polystyrene-divinylbenzene resin, carboxypolystyrene resin, chloromethylated polystyrene-divinylbenzene resin, hydroxymethyl polystyrene-divinylbenzene resin, 2-chlorotrityl chloride polystyrene resin, 4-benzyloxy-2'4'-dimethoxybenzhydrol resin (Rink Acid resin), triphenyl methanol polystyrene resin, diphenylmethanol resin, benzhydrol resin, succinimidyl carbonate resin, p-nitrophenyl carbonate resin, imidazole carbonate resin, polyacrylamide resin, 4-sulfamylbenzoyl-4'-methylbenzhydrylamine-resin (Safety-catch resin), 2-amino-2-(2'-nitrophenyl) propionic acid-aminomethyl resin (ANP Resin), p-benzyloxybenzyl alcohol-divinylbenzene resin (Wang resin), p-methylbenzhydrylamine-divinylbenzene resin (MBNA resin), Fmoc-2,4-dimethoxy-4'-(carboxymethyloxy)-benzhydrylamine linked to resin (Knorr resin), 4-(2',4'-Dimethoxyphenyl-Fmoc-aminomethyl)-phenoxy resin (Rink resin), 4-hydroxymethyl-benzoyl-4'-methylbenzhydrylamine resin (HMBA-MBHA Resin), p-nitrobenzophenone oxime resin (Kaiser oxime resin), and amino-2,4-dimethoxy-4'-(carboxymethyloxy)-benzhydrylamine handle linked to 2-chlorotrityl resin (Knorr-2-chlorotrityl resin). In one embodiment, the material used to form the polymeric resin is compatible with the solvent in which the analyte is dissolved. For example, polystyrene-divinylbenzene resin will swell within non-polar solvents, but does not significantly swell within polar solvents. Thus, polystyrene-divinyl benzene resin may be used for the analysis of analytes within polar or non-polar solvents. Alternatively, polystyrene-polyethylene glycol resin will swell with polar solvents such as water. Polystyrene-polyethylene glycol resin may be useful for the analysis of nonaqueous fluids.

In an embodiment, the polymeric resin may be in the form of polymer particles, such as small beads, or "microbeads." The size of the polymer particles and the structure of the support layer (for example, the structure of paper, including its porosity and permeability) affect the mobility of the polymer particles in the paper. For a given support layer material, polymer particles larger than a certain size will be effectively immobilized in the paper with respect to fluid flow by capillary action. This certain size can be determined experimentally. For example, for Whatman Grade 1 chromatography paper, one can show experimentally that 20 nm gold nanoparticles and 49 nm latex particles coated with a fluorescent yellow dye are mobile in a phosphate buffer saline solution flowing through the paper by capillary action from a wet region to a dry region of the paper. These particles are carried along to some extent with the capillary flow. Larger particles, such as 490 nm latex particles coated with a fluorescent yellow dye or 10 micron latex particles coated with Nile Red indicator do not move in the paper under the same conditions, and are effectively immobile with respect to fluid flow by capillary action. For other types of paper, or for other support layer materials, a skilled artisan may select different sizes of particles in order to make particles that are either mobile or immobile under capillary flow, according to the desired outcome. Polymeric resin may coat a magnetic core so that polymer particles of a selected size can be immobile under capillary flow, but also can be moved from place to place using an external magnet.

The chemically sensitive particle, in one embodiment, is capable of both binding the analyte(s) of interest and creating a detectable signal. In one embodiment, the particle will create an optical signal when bound to an analyte of interest. The use of such a polymeric bound receptors offers advantages both in terms of cost and configurability. Instead of having to synthesize or attach a receptor directly to a supporting member, the polymeric bound receptors may be synthesized en masse and distributed to multiple different supporting members. This allows the cost of the paper fluidic device, a major hurdle to the development of mass-produced environmental probes and medical diagnostics, to be reduced.

In one embodiment, a detectable signal may be caused by the altering of the physical or chemical properties of an indicator ligand bound to the receptor or the polymeric resin. In one embodiment, two different indicators are attached to a receptor or the polymeric resin. When an analyte is captured by the receptor, the physical distance between the two indicators may be altered such that a change in the spectroscopic properties of the indicators is produced. A variety of fluorescent and phosphorescent indicators may be used for this sensing scheme. This process, known as Forster energy transfer, is extremely sensitive to small changes in the distance between the indicator molecules.

In another embodiment, an indicator ligand may be preloaded onto the receptor. An analyte may then displace the indicator ligand to produce a change in the spectroscopic properties of the particles. In this case, the initial background absorbance is relatively small and it is enhanced when the analyte is present. The indicator ligand, in one embodiment, has a variety of spectroscopic properties which may be measured. These spectroscopic properties include, but are not limited to, ultraviolet absorption, visible absorption, infrared absorption, fluorescence, luminescence, and magnetic resonance. In one embodiment, the indicator is a dye having a strong fluorescence, or a strong ultraviolet absorption, or a strong visible absorption, or a combination of these physical properties. Examples of indicators include, but are not limited to, cyanine, carboxyfluorescein, ethidium bromide, 7-dimethylamino-4-methylcoumarin, 7-diethyl-amino-4-methylcoumarin, eosin, erythrosin, fluorescein, Oregon Green 488, pyrene, Rhodamine Red, tetramethyl-rhodamine, Texas Red, Methyl Violet, Crystal Violet, Ethyl Violet, Malachite green, Methyl Green, Alizarin Red S, Methyl Red, Neutral Red, o-cresolsulfonephthalein, o-cresolphthalein, phenolphthalein, Acridine Orange, B-naphthol, coumarin, and a-naphthionic acid. When the indicator is mixed with the receptor, the receptor and indicator interact with each other such that the above mentioned spectroscopic properties of the indicator, as well as other spectroscopic properties may be altered. The nature of this interaction may be a binding interaction, wherein the indicator and receptor are attracted to each other with a sufficient force to allow the newly formed receptor-indicator complex to function as a single unit. The binding of the indicator and receptor to each other may take the form of a covalent bond, an ionic bond, a hydrogen bond, a van der Waals interaction, or a combination of these bonds.

The indicator may be chosen such that the binding strength of the indicator to the receptor is less than the binding strength of the analyte to the receptor. Thus, in the presence of an analyte, the binding of the indicator with the receptor may be disrupted, releasing the indicator from the receptor. When released, the physical properties of the indicator may be altered from those it exhibited when bound to the receptor. The indicator may revert back to its original structure, thus regaining its original physical properties. For example, if a fluorescent indicator is attached to a particle that includes a receptor, the fluorescence of the particle may be strong before treatment with an analyte containing fluid. When the analyte interacts with the particle, the fluorescent indicator may be released. Release of the indicator may cause a decrease in the fluorescence of the particle, since the particle now has less indicator molecules associated with it.

In an embodiment, the analyte molecules in the fluid may be pretreated with an indicator ligand. Pretreatment may involve covalent attachment of an indicator ligand to the analyte molecule. After the indicator has been attached to the analyte, the fluid may be passed over the sensing particles. Interaction of the receptors on the sensing particles with the analytes may remove the analytes from the solution. Since the analytes include an indicator, the spectroscopic properties of the indicator may be passed onto the particle. By analyzing the physical properties of the sensing particles after passage of an analyte stream, the presence and concentration of an analyte may be determined. For example, the analytes within a fluid may be derivatized with a fluorescent tag before introducing the stream to the particles. As analyte molecules are adsorbed by the particles, the fluorescence of the particles may increase. The presence of a fluorescent signal may be used to determine the presence of a specific analyte. Additionally, the strength of the fluorescence may be used to determine the amount of analyte within the stream.

A variety of natural and synthetic receptors may be used. The synthetic receptors may come from a variety of classes including, but not limited to, polynucleotides (e.g., aptamers), proteins (e.g., enzymes and antibodies), peptides, peptide nucleic acid, synthetic receptors, polymeric unnatural biopolymers (e.g., polythioureas, polyguanidiniums), and imprinted polymers. Natural based synthetic receptors include receptors which are structurally similar to naturally occurring molecules. Polynucleotides are relatively small fragments of DNA or RNA which may be derived by sequentially building a DNA or RNA sequence. Peptides may be synthesized from amino acids. Unnatural biopolymers are chemical structures which are based on natural biopolymers, but which are built from unnatural linking units. Unnatural biopolymers such as polythioureas and polyguanidiniums may be synthesized from diamines (i.e., compounds which include at least two amine functional groups). These molecules are structurally similar to naturally occurring receptors, (e.g., peptides). Some diamines may, in turn, be synthesized from amino acids. The use of amino acids as the building blocks for these compounds allows a wide variety of molecular recognition units to be devised. For example, the twenty natural amino acids have side chains that possess hydrophobic residues, cationic and anionic residues, as well as hydrogen bonding groups. These side chains may provide a good chemical match to bind a large number of targets, from small molecules to large oligosaccharides.

In an embodiment, the indicator ligand may be incorporated into synthetic receptors during the synthesis of the receptors. The ligand may be incorporated into a monomeric unit, such as a diamine, that is used during the synthesis of the receptor. In this manner, the indicator may be covalently attached to the receptor in a controlled position. By placing the indicator within the receptor during the synthesis of the receptor, the positioning of the indicator ligand within the receptor may be controlled. This control may be difficult to achieve after synthesis of the receptor is completed.

Figure 6A:
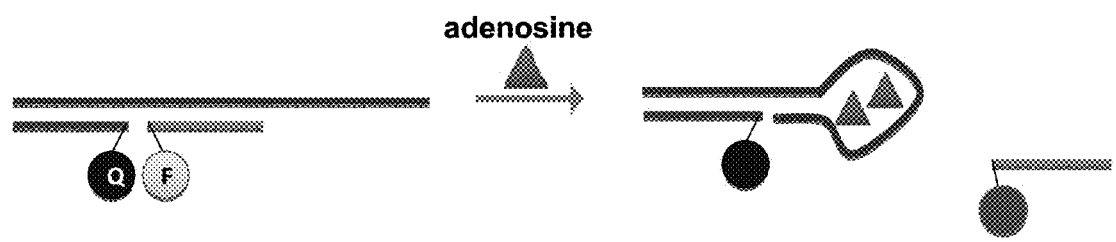
FIG. 6A depicts a schematic diagram of a nucleic acid based testing method.

An example of a particle based detection system is shown in FIG. 6A. In this scheme, an aptamer strand (purple strand), which is capable of binding the analyte (e.g., adenosine), is coupled to a particle. A fluorophore strand (orange strand) and a quencher strand (purple) are coupled to the aptamer prior to testing. The quencher (Q) quenches the fluorescence of the fluorophore (F) in the absence of the analyte (adenosine). When adenosine is present, the adenosine binds to the aptamer releasing the fluorophore strand. Release of the fluorophore strand produces a fluorescent signal that can be used to determine the presence and concentration of the analyte.

The sequence of an exemplary aptamer strand, quencher strand (Q) and fluorophore strand (F) for analysis of adenosine is depicted below:

[SEQ ID NO: 1]
3' TGA GTA GAC ACT(F)

[SEQ ID NO: 2]
TCT CTT GGA CCC(Q) 5'

[SEQ ID NO: 3]
5' ACT CAT CTG TGA   AGA GAA CCT GGG GGA GTA TTG CGG AGG AAG GT 3'

The italicized portion of the aptamer strand is the portion that binds to adenosine.

Figure 6B:
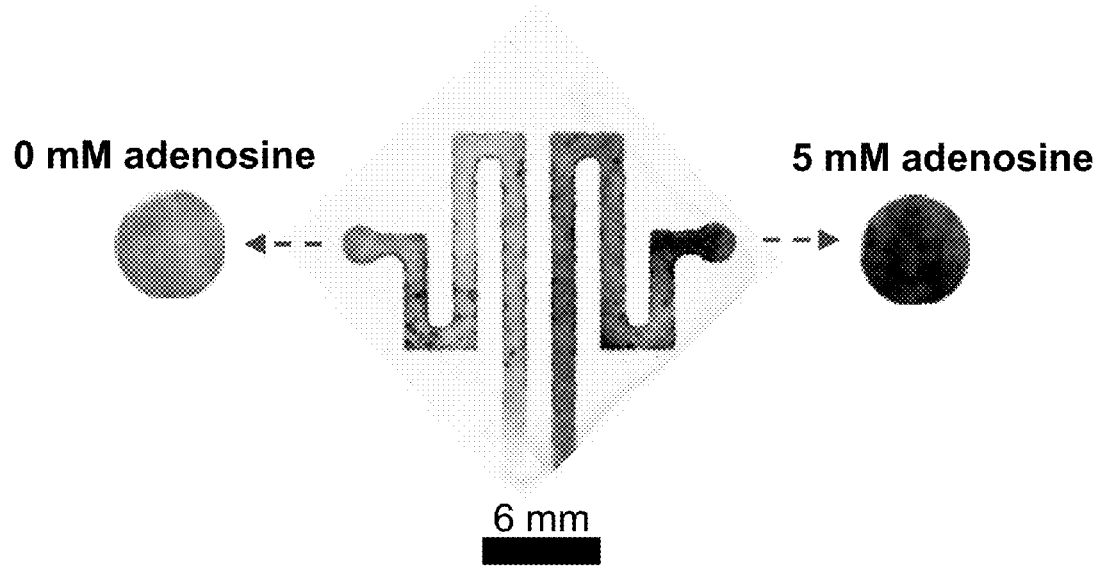
FIG. 6B depicts channels from a fluidic analytical device which were used during the nucleic acid based testing method of FIG. 6A.
Figure 6C:
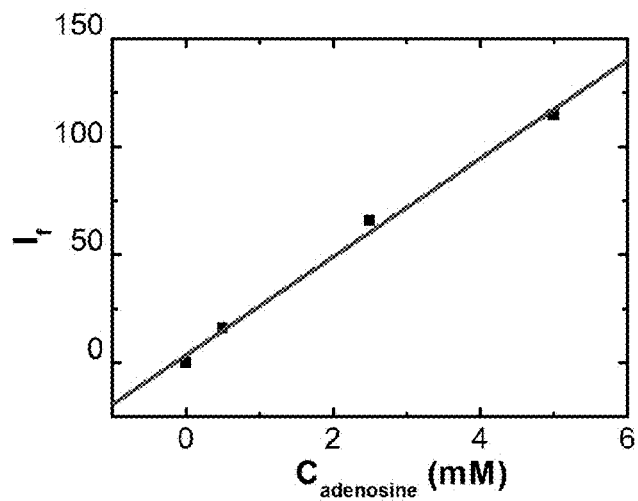
FIG. 6C depicts a concentration plot based on the nucleic acid testing method of FIG. 6A.

To demonstrate the function of aptamer probe using an oPAD, the fluorescent adenosine aptamer sensor was tested using a device. An embodiment of the device is depicted in FIG. 6B, in which two channels are formed, having a serpentine pattern. A serpentine pattern is used for the channel to increase the contact time of the analyte fluid with the adenosine detection particles, which are deposited in the channel, forming a zone through which the target molecules will flow. The contact time of the target molecules with the chemically sensitive particles is the length of the zone divided by the flow rate through the channel. In an embodiment, the fluorescent probe cyanine 5 (Cy5) is used. Upon binding to adenosine, the fluorescence from Cy5 is enhanced by release of the fluorophore strand and separation of Cy5 from the quencher. As shown in FIG. 6B, two separate channels were preloaded with 15 µL aptamer solution, containing 0.32 µM aptamer strand, 0.2 µM fluorophore strand and 0.4 µM quencher strand, and dried in air. The right channel was filled with 15 µL 0.01 M PBS buffer (pH 7.4) containing 5 mM adenosine, and the left channel is filled with 15 µL of adenosine-free PBS. After reacting for 15 min, the fluorescence from both channels was measured by a fluorescent scanner. The darker color in the right channel represents higher fluorescent intensity. A plot of fluorescent intensity ($I_f$) versus the concentration of adenosine ($C_{adenosine}$) in the sample is shown in FIG. 6C. The plot was generated by measuring the fluorescent intensity in the right circular reservoir and subtracting from this value the fluorescent intensity measured in the left circular reservoir. As shown in FIG. 6B, enhanced fluorescence was observed in the right circular reservoir when adenosine was added to the right channel. This test was repeated with different concentrations of adenosine to generate the plot depicted in FIG. 6C. As shown in FIG. 6C, a linear relationship between the fluorescence intensity and the adenosine concentration is observed from 0.5 mM to 5 mM.

Figure 7:
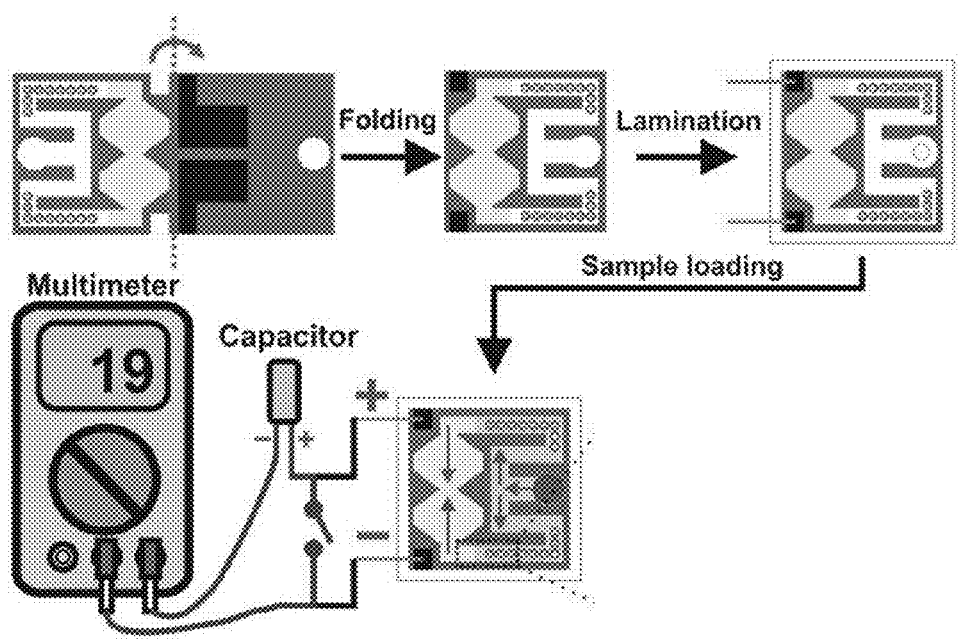
FIG. 7 depicts a schematic diagram of a fluidic analytical device that includes reservoirs for electrochemical testing.

In another embodiment, a self-powered origami paper analytical device (oPAD) may use an aptamer to recognize an analyte by monitoring the change in electrical properties of an electroactive redox couple. The device is self-powered in that it self-generates an electrical signal that can be measured with an appropriate electrical measurement device. The principle of the device is illustrated in FIG. 7. The device is printed on a single piece of paper and folded into a three-dimensional (3D) configuration as was described for FIG. 2. Additionally during that process, following the patterning process, the patterned paper was placed on a flat glass surface, and then covered with a stencil. An aliquot of carbon ink was dropcast on the stencil. A coating rod was used to coat the carbon ink uniformly onto the patterned paper through the stencil. To cure the carbon ink, the stencil was removed from the paper, and the paper was placed in an oven at 80° C. for 30 min. The cured carbon ink may function as electrodes on the device. The device was later laminated in plastic.

An aliquot of sample that contains an analyte of interest is loaded at the inlet, split into two channels, and then directed to microbeads entrapped within the channels. In one channel (e.g., the right channel) said microbeads (purple) are chemically sensitive particles that have bound receptor molecules. These receptor molecules interact with the analyte of interest by releasing a glucose oxidase (GOx)-labeled DNA strand (aptamer) that may then flow downstream. In the absence of the analyte, the GOx-labeled DNA strand stays bound to the microbeads. No aptamer is present on the microbeads (blue) in the left channel. The split fluids terminate in an hourglass-shaped, two-compartment electrochemical cell (yellow portion). The waist of the hourglass shape serves as a salt bridge between the two half cells, which might or might not be necessary for operation of the device. In one of the half cells, GOx catalyzes the oxidation of glucose, which in turn results in conversion of $Fe(CN)_6^{3-}$ to $Fe(CN)_6^{4-}$. This change in the relative concentrations of $Fe(CN)_6^{3-}$ and $Fe(CN)_6^{4-}$ yields an electrochemical cell, more specifically a concentration cell. The change in voltage difference between the two half cells can be measured directly, or the voltage can be converted to a current. In either case, the voltage or current can be measured and correlated with the concentration of the analyte. In some embodiments, the electrochemical cell can be used to charge a capacitor. When the switch is closed, the capacitor discharges through the electrical measuring device (e.g., a multimeter). The capacitor provides a large instantaneous current, in effect an amplified current, and hence a higher signal-to-noise ratio than a direct current measurement.

Figure 8A:
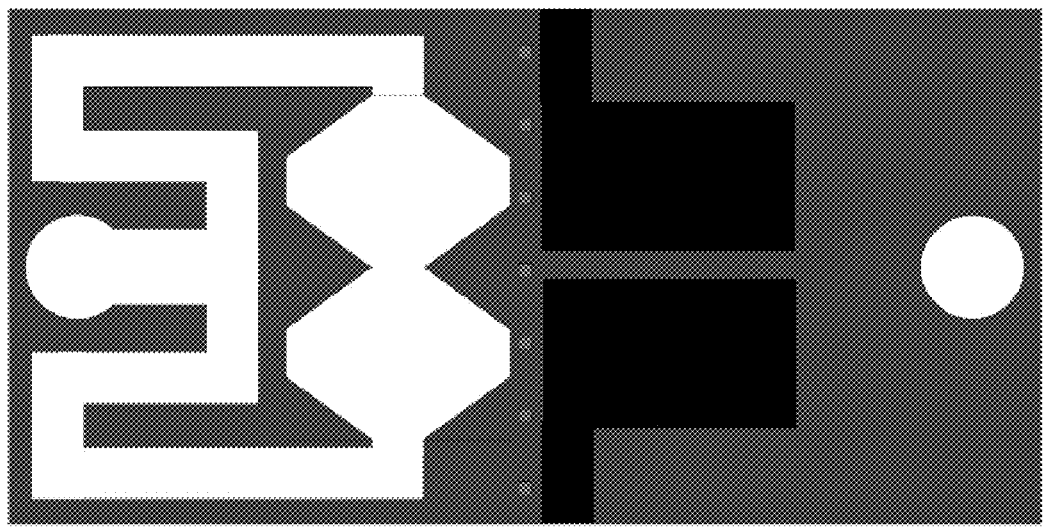
FIG. 8A depicts a template for a fluidic analytical device that includes reservoirs for electrochemical testing and electrodes.
Figure 8B:
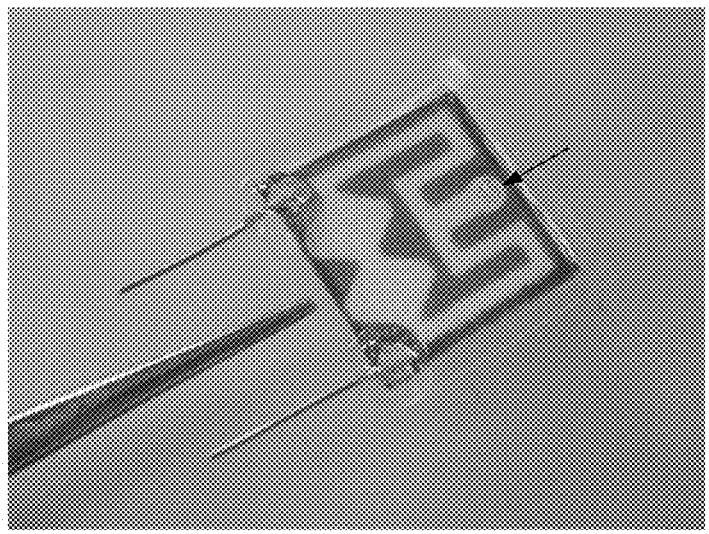
FIG. 8B depicts an assembled fluidic analytical device that includes reservoirs and electrodes for electrochemical testing.

An example of a paper fluidic electrochemical cell is depicted in FIGS. 8A and 8B. A paper fluidic device may be formed from two layers as shown in FIG. 8A. On the first layer (left side), an inlet, and two split channels were fabricated by wax printing. On the second layer (right side), two electrodes were fabricated by screen printing conductive ink (black regions) onto the paper. Although any electrical conductor could be used, preferably carbon ink is used. An additional fluidic inlet is also present on the second layer, and it can be used for adding additional sensing layers. When the paper is folded at the predetermined fold line (blue dotted line), the electrodes contact the end of the fluidic channel where the two split channels recombine to form two half cells connected by a thin fluidic channel that acts as a salt bridge. This strategy avoids direct printing of the electrodes onto the channel architecture, which would render the channels hydrophobic due to the binder present in the carbon ink.

One embodiment of the invention comprises active zones, for example electrodes, that are fabricated on the support layer, spatially separated from fluidic channels and reservoirs. By folding the support layer, the electrodes are brought into contact with the fluidic channels and reservoirs. Another embodiment of the invention comprises active zones that are fabricated on a separate layer from the main fluidic channel layer. A water-impermeable barrier may span a channel, preventing passage of liquid directly down the channel, and providing a second layer conduction zone that contains the active site components overlapping both sides of the impermeable cross-channel barrier. In another embodiment of the invention, the folded support layer aligns the channels of one layer with the impermeable channel walls of the adjacent layer, providing the benefit of many parallel channels and test zones, which could reduce or eliminate cross-contamination between layers, or be used for multiplexed testing.

To test the device, an electrochemical concentration cell was constructed using GOx, which was preloaded in one of the channels. A solution containing 12 µL of 100 mM glucose and 100 mM $Fe(CN)_6^{3-}$ in 0.01 M PBS buffer (pH 6.0) was loaded into both halves of the electrochemical cell. After drying in the dark, the device was folded and then encapsulated in plastic by impulse edge thermal lamination. As shown in FIG. 8B, the oPAD was fully enclosed with a small opening made on top for sample loading (indicated by the arrow) and two wires, preferably copper wires, connected to the electrodes, preferably carbon electrodes. Note that lamination enables the vertical connection between the channels of adjacent layers, which eliminates the use of the metal clamp described above. 20 µL 0.01 M PBS buffer (pH 7.4) was loaded at the inlet of the oPAD. After 10 min, when the fluid recombined at the end of the fluidic channel, the oPAD was placed onto a bread-board. The electric circuit on the breadboard was designed to measure the current generated by the oPAD using a digital multimeter (DMM) while simultaneously accumulating the charge on the capacitor. It is contemplated that optionally the capacitor may be integrated into the laminated package. It is contemplated that a capacitor, optionally integrated with or on-board the device, could allow the signal from the device to be read at any time during an extended period following completion of a test. Upon closing the switch, the capacitor discharges nearly instantaneously, and the maximum current is recorded by the DMM. The magnitude of the current increased with increasing amounts of GOx. Due to the amplification, the sensitivity (4.1 µA/pmol) increased by 15.5-fold using a capacitor compared to a simple current measurement (0.26 µA/pmol).

Figure 9A:
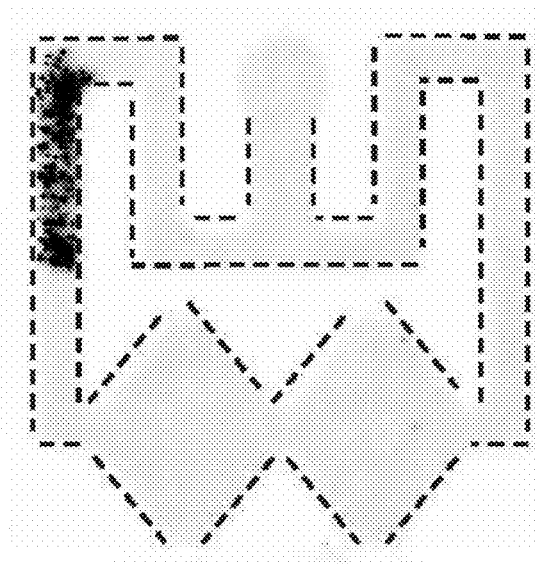
FIGS. 9A-9B depict the position of chemically sensitive particles in a channel of a fluidic analytical device.
Figure 9B:
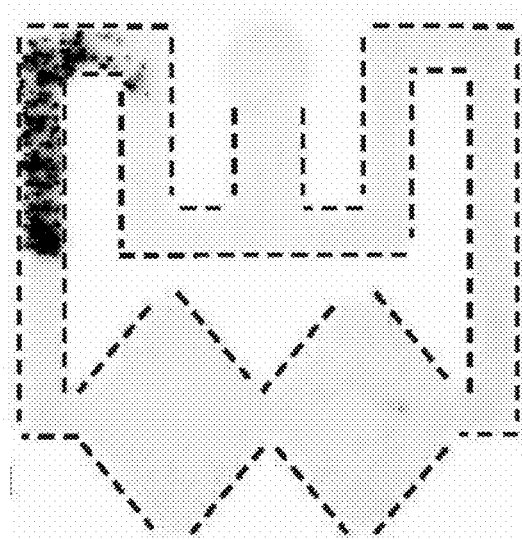

Biotin-labeled aptamer was immobilized on 10 µm-diameter polystyrene (PS) microbeads functionalized on their surface with streptavidin. It was possible to observe the location of the microbeads, because they contained fluorescent indicator Nile Red. A 0.1 µL aliquot of the 0.25% (w/v) microbeads was added to one of the channels and allowed to dry. To ensure that the microbeads did not move in the paper channels, the following simple experiment was run. First, the entire device was imaged in a fluorescence scanner to locate the beads (FIG. 9A). Next, a PBS solution (0.01 M, pH 7.4) was added to the device inlet and allowed to flow to its end. Finally, the device was imaged a second time (FIG. 9B). The results show minimal (and acceptable) low displacement after exposure to the buffer solution.

Heterogeneous assays generally require longer incubation times than homogeneous assays due to reduced mass transfer of reagents to the immobilized probes. Longer assay times can be a problem for paper devices due to solvent evaporation, but this issue has been addressed by encapsulating the device in an impermeable enclosure. For example, pressure-sensitive adhesives or printer toner have been used for this purpose. We used a plastic envelope sealed with an impulse thermal edge laminator that only applies heat to the edge of the plastic. This approach avoids adhesives, which can lead to contamination or nonspecific adsorption of reagents or targets, and heat-induced deactivation. We found that PBS solution kept flowing and wet in the enclosed device at 37° C. for >2 h without drying.

For electrochemical read-out, we used 5' biotin-modified DNA (bDNA). The biotin group was used to link streptavidin-labeled GOx (sGOx). The sequence of an exemplary aptamer strand, biotin strand and streptavidin labeled $GO_x$ for analysis of adenosine using an electrochemical cell is depicted below:

[SEQ ID NO: 4]
3' Biotin - $A_6$ - $A_6$ - TGA GTA GAC ACT TCT CTT GGA CCC - A12 - biotin streptavidin - Gox

[SEQ ID NO: 5]
5' - $T_6$ - ACT CAT CTG TGA AGA GAA CCT GGG GGA GTA TTG CGG AGG AAG GT 3'

Figure 10:
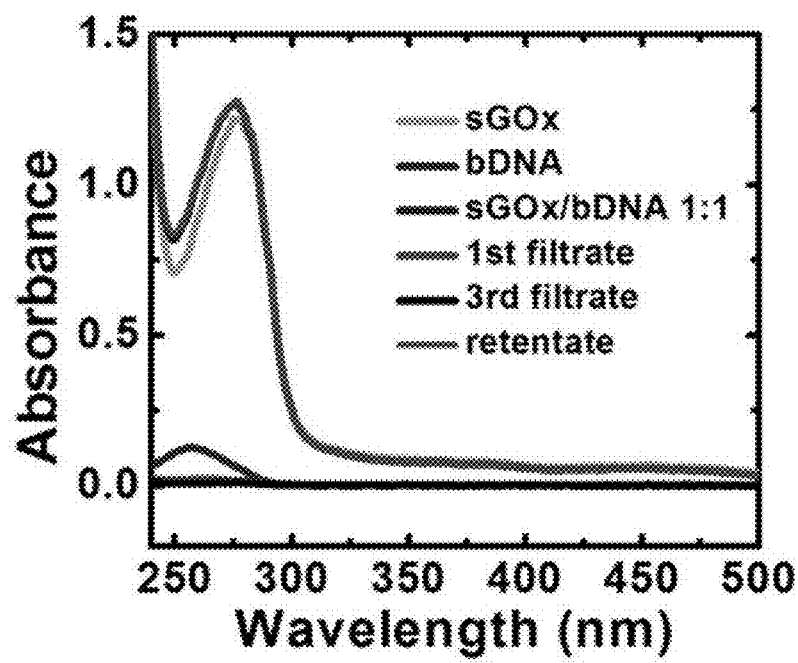
FIG. 10 depicts UV plots collected from a nucleic acid based fluidic analytical device.

UV-vis spectroscopy was used to characterize the product (FIG. 10). The characteristic absorptions of protein and DNA are at 280 nm and 260 nm, respectively. For a solution containing both sGOx and bDNA at 1:1 ratio, the absorption of sGOx at 280 nm was observed and the adsorption at 260 nm was higher than that of the solution containing only sGOx, indicating the presence of bDNA. To separate free bDNA from sGOx-labeled bDNA, we filtered the solution for 30 minutes at 4000 rpm using a 50K nominal molecular weight limit (NMWL) centrifugal filter for three times. The adsorption of the retentate at 260 nm was similar to the one before filtration, and was obviously higher than that of the solution containing only sGOx, which demonstrates the binding of the bDNA to the sGOx. Due to the fact that the absorption at 260 nm for filtrate is very small, almost all bDNA binds to sGOx considering the excess binding sites on sGOx, and the ratio of sGOx to bDNA in the final product is about 1:1.

Figure 11:
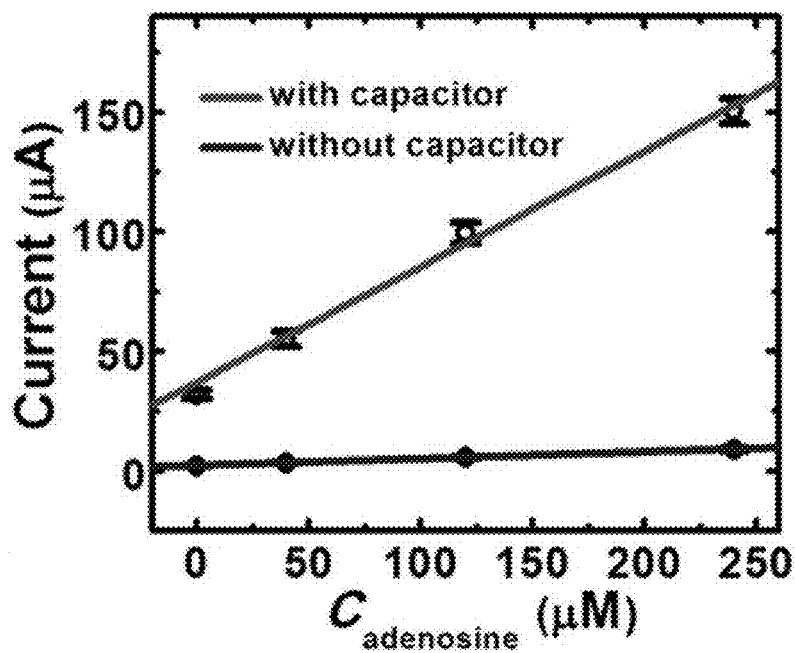
FIG. 11 depicts the current, arising from electrochemical reactions, as a function of the analyte concentration measured in a fluidic analytical device that includes reservoirs and electrodes for electrochemical testing.

To integrate the GOx labeled aptamer sensor on the oPAD, three solutions of 20 µL each containing 17 µM GOx-DNA strand, 25 µM aptamer strand and 25 µM biotin-DNA strand respectively were mixed together to form an aptamer solution. The aptamer solution was mixed with 20 µL of streptavidin labeled microbeads solution. After reaction in the dark for 24 hours, the solution was dropcast in one split channel, allowed to dry for 10 minutes, and then washed with 0.01 M PBS buffer (pH 7.4) containing 0.1% bovine serum albumin. Similar to the previous procedure to construct the electrochemical concentration cell using GOx, the substrate solution was loaded at the end of the channel, and dried in the dark. After folding, thermal lamination, and attaching copper wires, 20 µL of sample was introduced to the inlet for detecting adenosine. After about 10 min, when the solution recombines at the end of the channel, the oPAD was placed onto a breadboard to measure the current. As shown in FIG. 11, the current increased with increasing adenosine concentration. The detection limit, calculated as 3-times standard deviation of the blank divided by the slope, is 11.8 µM with the capacitor amplification. The sensitivity (0.483 µA/µM) increased by 16.9-fold compared to that without amplification (0.0285 µA/µM).

As shown above, the devices described herein provide a number of advantages. First, the aptamer is immobilized on microbeads trapped within the paper fluidic channel. This greatly simplifies probe introduction, compared to direct immobilization on paper, because existing immobilization and characterization methods can be used for a range of different probe families including aptamers, DNAzymes, and antibodies. Second, as configured in this device, bead immobilization eliminates the need for a washing step in the operation of the device. Third, aptamers and even nucleic acid probes can be used in a paper fluidic device. Although they have been used on test strips, no application in paper fluidic devices have been reported. The use of aptamers allows a wide range of targets to be detected, including those that are not immunogenic, like the adenosine target in our example. Moreover, nucleic acid probes are generally significantly more stable than those based on proteins. Fourth, the transducer is based on an electrochemical cell, which acts as a battery to charge a capacitor that is subsequently read-out using a DMM. The latter has a very wide dynamic range, and the use of the capacitor results in a quantitative response that yields a 17-fold enhancement compared to a direct current measurement. Finally, the device is encapsulated in plastic using impulse edge thermal lamination, which solves many problems, including fluid evaporation, reagent deactivation, and device contamination.

Method for Detection and Quantification of Antibodies

The effectiveness of an immunization regimen for an individual can be accessed by determining the level of anti-disease antibodies in the individual. For example, to determine the effectiveness of tetanus vaccines, the presence and concentration of anti-tetanus antibodies in the patient can be determined. Many methods that are used to determine specific antibody concentrations in human subject rely on expensive equipment and chemical reagents. In order to determine the effectiveness of immunization programs in many countries, especially in developing nations, there is a need to rapidly and cheaply assess individual immunity to infectious diseases.

In one embodiment, the concentration of antibodies in a subject may be determined by converting an antibody reaction with a chemical agent into a glucose signal which correlates to the concentration of antibody. The glucose signal may be read using a potentiometer (as discussed above) or preparing a test strip which can be read in a personal glucose meter. A "glucose signal" means a measureable amount or concentration of glucose.

In one embodiment a chemically sensitive particle may be designed to capture one or more antibodies of interest. For example, a chemically sensitive particle may include one or more antigens that evoke the production of one or more antibodies of interest. The antigens may be coupled to a polymeric support (e.g., a bead). During use, when a sample is introduced to the chemically sensitive particles, antibodies to the supported antigens are captured by the chemically sensitive particle. While any antigen-antibody combination may be used in a detection system, of particular interest are detection system for polio, measles, hepatitis A, hepatitis B, tetanus, cholera, yellow fever, typhoid, diphtheria, tuberculosis, plague, rabies, influenza, and dengue virus.

Once captured, there are various techniques that can be used to determine the presence and quantity of antibodies. In one embodiment, the quantification of an antibody of interest (the "primary antibody") may be done using a visualization antibody (the "secondary antibody"). In an embodiment, the secondary antibody may be an antibody that recognizes and complexes with the primary antibody. The secondary antibody may include a tag that provides a signal indicating the presence of the primary antibody. Examples of tags include fluorescent or colorimetric tags, electrochemically active molecules or particles, or enzymes or metal particles that catalyze a chemical transformation that is easily detectable. A tag is sometimes referred to as a label. Some tags may be catalysts. Metal particles may be used as tags. A metal-particle tag might be catalytic, or it might directly participate in a chemical reaction or be electrochemically active. For example Ag particles may be used as tags, whereby a signal is provided by dissolution of the Ag particle.

Figure 12:
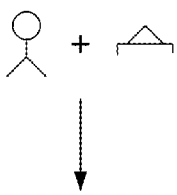
FIG. 12 depicts a schematic diagram of a method of detecting antibodies in a sample.
Figure 12:
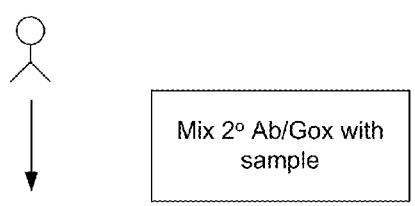
Figure 12:
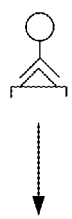
Figure 12:
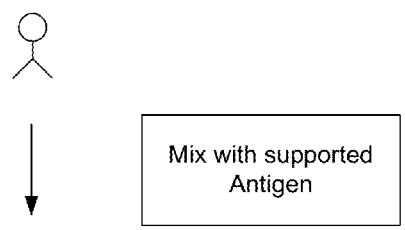
Figure 12:
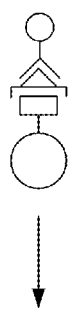
Figure 12:
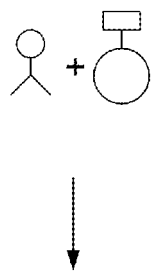
Figure 12:
Figure 12:
Figure 12:
Figure 12:
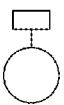

In one embodiment, the presence and quantity of a primary antibody may be determined using a secondary antibody having an enzyme coupled to the secondary antibody. For example, the enzyme glucose oxidase (GOx) will catalyze the oxidation of glucose to hydrogen peroxide and gluconic acid. This transformation may be used to quantify the primary antibodies. An embodiment of a detection scheme, which relies on the enzyme glucose oxidase, is depicted in FIG. 12. The process uses a secondary antibody which is linked to glucose oxidase (2° Ab/GOx) to aid in the detection and quantification of the antibody of interest (1° Ab). In the initial step, the sample that is being tested is mixed with 2° Ab/GOx. If the 1° Ab is present, the antibody will form a complex with the 2° Ab/GOx, as shown in the left column. If no (or very little) 1° Ab is present, no complex is formed. In the second step, the separation of the complexed 1° Ab is initiated by reacting the sample, after reaction with 2° Ab/GOx, with a supported antigen for the 1° Ab. When the 1° Ab is present, the complexed antibody will couple to the supported antigen to form a complex which includes the 2° Ab/GOx and is coupled to the support (e.g., a bead). For example, if the target 1° Ab is for tetanus, the supported antigen could be tetanus toxoid immobilized on beads. When 1° Ab is not present, then the 2° Ab/GOx remains in solution and is not complexed to the support. In the final step of the sample preparation, the beads are separated from the reaction mixture to provide a testing solution that either does not include any 2° Ab/GOx (left column) or which includes at least some uncomplexed 2° Ab/GOx (right column). The amount of 2° Ab/GOx that is collected at the end of the testing process is therefore related to the amount of 1° Ab present in the sample. If a known amount of 2° Ab/GOx is present in the initial step, the amount that is missing at the end of processing is proportional to the amount of 1° Ab present in the sample. The more 2° Ab/GOx present at the end of the process, the less the amount of 1° Ab was present in the sample.

Figure 13:
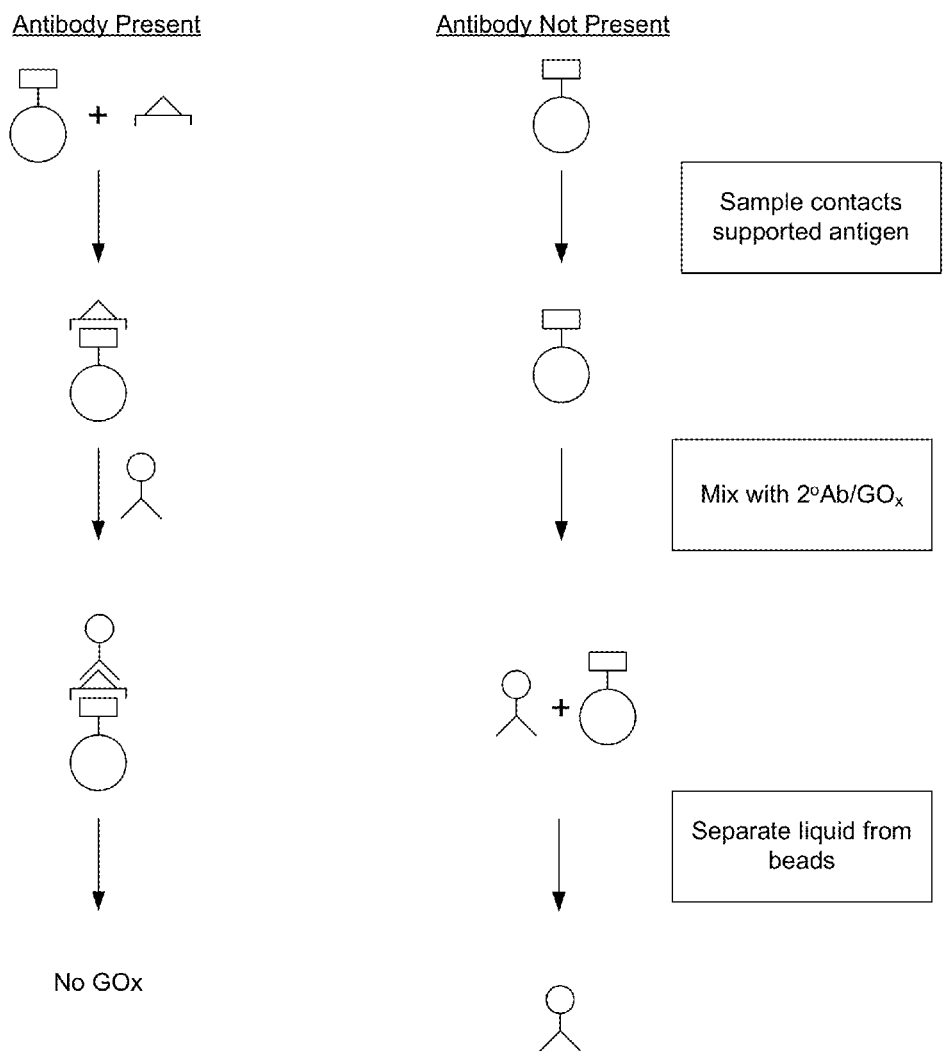
FIG. 13 depicts a schematic diagram of an alternate method of detecting antibodies in a sample.

In another embodiment of a detection scheme that relies on a metal or an enzyme catalyst, for example glucose oxidase, is depicted in FIG. 13. We shall describe this embodiment here using the enzyme glucose oxidase (GOx) as an example of a catalyst. However, the role played by GOx in this embodiment could also be played by a different enzyme, or by a catalytic particle such as metal or metal oxide, or by an electrochemically active particle such as a Ag particle. The process uses a secondary antibody which is linked to the enzyme glucose oxidase (2° Ab/GOx) to aid in the detection and quantification of the antibody of interest (1° Ab). In the initial step, the sample that is being tested is contacted with a supported antigen for 1° Ab. For example, if the target 1° Ab is for tetanus, the supported antigen could be tetanus toxoid immobilized on beads. If the 1° Ab is present, the antibody will form a complex with the supported antigen, as shown in the left column of FIG. 13. If no (or very little) 1° Ab is present, no complex is formed. Any non-specifically bound material may be removed by washing. In the second step, a secondary antibody linked to glucose oxidase (2° Ab/GOx) is introduced to contact the supported antigen. When the 1° Ab is present as a complex on the supported antigen, the 2° Ab/GOx will couple to the 1° Ab to form a complex which includes the 2° Ab/GOx, 1° Ab, and antigen all coupled to the support (e.g., a bead). When 1° Ab is not present, then the 2° Ab/GOx remains in solution and is not complexed to the support. In the final step of the sample preparation, the beads are separated from the reaction mixture to provide a testing solution that either does not include any 2° Ab/GOx (left column) or which includes at least some uncomplexed 2° Ab/GOx (right column). The amount of 2° Ab/GOx that is collected at the end of the testing process is therefore related to the amount of 1° Ab present in the sample. If a known amount of 2° Ab/GOx is present in the second step, the amount that is missing at the end of processing is proportional to the amount of 1° Ab present in the sample. The more 2° Ab/GOx present at the end of the process, the less the amount of 1° Ab was present in the sample.

A number of techniques can be used to identify and quantify the amount of 2° Ab/enzyme that is present at the end of the processing steps. The enzyme that is coupled to the antibody catalyzes a chemical reaction on an enzymatic substrate. Thus, in one embodiment, after the beads are separated from the sample processing the liquid obtained is reacted with a known amount of enzymatic substrate. If 2° Ab/enzyme is present in the liquid, the enzymatic substrate will be transformed into reaction products and the amount or concentration of enzymatic substrate will be reduced. By determining how much enzymatic substrate remains, or by determining the amount produced of at least one reaction product, the amount of 1° Ab can be inferred. In this testing scheme, the remaining enzymatic substrate amount or concentration is directly related to the amount of antibody in the original test sample.

More specifically, a number of techniques can be used to identify and quantify the amount of 2° Ab/GOx that is present at the end of the processing steps. The GOx that is coupled to the antibody catalyzes the oxidation of glucose to hydrogen peroxide and gluconic acid. Thus, in one embodiment, after the beads are separated from the sample processing the liquid obtained is reacted with a known amount of glucose. If 2° Ab/GOx is present in the liquid, glucose will be transformed into gluconic acid and hydrogen peroxide and the amount or concentration of glucose will be reduced. By determining how much glucose remains, or by determining the amount of hydrogen peroxide produced, the amount of 1° Ab can be inferred. In this testing scheme the reduction in glucose is directly related to the amount of antibody in the original test sample. High glucose or low peroxide indicates the presence of 1° Ab in the original sample. Low glucose or high peroxide indicates absence of 1° Ab in the original sample. Either of the glucose concentration or the peroxide concentration can be used as quantitative measures of 1° Ab concentration in the original sample, if the amount of 2° Ab used in the testing scheme is known.

Figure 14:
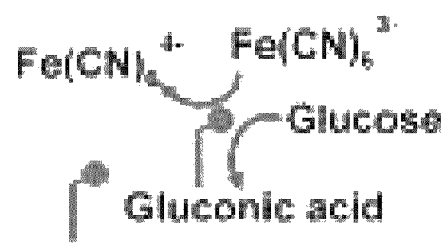
FIG. 14 depicts a schematic diagram of a redox reaction between GOx, glucose, and $Fe(CN)_6^{3-}$.

The amount of glucose in a test sample can be determined using a number of different techniques. For example, the mixture of glucose reacted with the test sample supernatant can be applied to a commercially obtained test strip and placed into a glucose test strip reader. The test reader will provide a number which corresponds to the concentration of glucose in the sample. This number can then be converted into a value which represents the concentration of antibodies in the test sample. In an alternate embodiment, a change in electrical properties of an electroactive redox couple may be used to determine the concentration of glucose, and thus the concentration of antibodies. One example of an electroactive redox couple is $Fe(CN)_6^{3-}/Fe(CN)_6^{4-}$. GOx catalyzes the oxidation of glucose, which in turn results in conversion of $Fe(CN)_6^{3-}$ to $Fe(CN)_6^{4-}$. This change in the relative concentrations of $Fe(CN)_6^{3-}$ and $Fe(CN)_6^{4}$ yields an electrochemical cell, more specifically a concentration cell. The change in current can then be measured and correlated with the concentration of GOx that was present in the reaction. The amount of GOx in the sample is proportional to the amount of antibody present in the original sample. FIG. 14 depicts a schematic diagram of this redox reaction.

One skilled in the art will recognize that the role of the GOx enzyme in the process may be played by other compounds or materials, with similar results. The GOx enzyme as shown in FIGS. 12 and 13 is functionally a tag on the 2° Ab. This function could be carried out using other compounds or materials that are known to one skilled in the art, and we do not intend the example of GOx, or even of enzymes in general, to be limiting. For example, suitable tags are envisioned as other enzymes, aptamers, catalysts, nanoparticles, fluorescent chemicals, radio labeled chemicals, indicator chemicals, and other materials known in the art. As an illustration of one of these other examples, the smaller circles in FIGS. 12 and 13 that represent GOx could alternatively represent a catalytic nanoparticle, for example a platinum nanoparticle or a silver nanoparticle. In that case, another embodiment of a detection scheme relies on a catalytic nanoparticle, for example a nanoparticle that comprises platinum. The process uses a secondary antibody which is linked to the nanoparticle (2° Ab/NP by analogy to 2° Ab/GOx in FIG. 13) to aid in the detection and quantification of the antibody of interest (1° Ab). In the initial step, the sample that is being tested is contacted with a supported antigen for 1° Ab. For example, if the target 1° Ab is for tetanus, the supported antigen could be tetanus toxoid immobilized on beads. If the 1° Ab is present, the antibody will form a complex with the supported antigen, as shown in the left column of FIG. 13. If no (or very little) 1° Ab is present, no complex is formed. Any non-specifically bound material may be removed by washing. In the second step, a secondary antibody linked to a nanoparticle (2° Ab/NP) is introduced to contact the supported antigen. When the 1° Ab is present as a complex on the supported antigen, the 2° Ab/NP will couple to the 1° Ab to form a complex which includes the 2° Ab/NP, 1° Ab, and antigen all coupled to the support (e.g., a bead). When 1° Ab is not present, then the 2° Ab/NP remains in solution and is not complexed to the support. In the final step of the sample preparation, the beads are separated from the reaction mixture to provide a testing solution that either does not include any 2° Ab/NP (left column) or which includes at least some uncomplexed 2° Ab/NP (right column). The amount of 2° Ab/NP that is collected at the end of the testing process is therefore related to the amount of 1° Ab present in the sample. If a known amount of 2° Ab/NP is present in the second step, the amount that is missing at the end of processing is proportional to the amount of 1° Ab present in the sample. The more 2° Ab/NP present at the end of the process, the less the amount of 1° Ab was present in the sample.

A number of techniques can be used to identify and quantify the amount of 2° Ab/NP that is present at the end of the processing steps, and thereby infer the amount of 1° Ab present in the original sample. The nanoparticle that is coupled to the antibody may catalyze a chemical reaction, for example dissociation of peroxide by Pt nanoparticles. Alternatively, the nanoparticle may be captured or immobilized on and electrode surface where it can catalyze an electrochemical reaction and generate an electrochemical signal. Thus, in one embodiment, after the beads are separated from the sample processing the liquid obtained is reacted with a known amount of at least one reactant. If 2° Ab/NP is present in the liquid, the reactant will be transformed into at least one reaction product, and the amount or concentration of the reactant will be reduced. By determining how much reactant remains, or by determining the amount produced of at least one reaction product, the amount of 1° Ab can be inferred. In this testing scheme, the remaining reactant amount or concentration is directly related to the amount of antibody in the original test sample. More specifically, the reactant could be peroxide, which would be dissociated by Pt nanoparticles to produce $HOO^-$, a strong nucleophile, which can be simply detected by a number of methods. Alternatively, the Pt nanoparticles could be captured on an otherwise inert conductive electrode surface and be detected electrochemically by electrochemical amplification. Electrochemical amplification can occur when a catalytic nanoparticle collides with and sticks to an electrode that itself does not carry out an indicator reaction of interest (e.g., proton reduction or hydrazine oxidation). An inert electrode (such as a C or Au microelectrode), is held at a potential where the indicator reaction does not occur. However when a catalytic nanoparticle (such as a Pt nanoparticle) collides with it, the indicator reaction can then occur at a rate determined by the concentration of reactant in solution, its diffusion coefficient, the potential, and the available reaction area on the nanoparticle. This generates an detectable electrochemical signal, such as a current, that can be correlated to the concentration or amount of nanoparticles, and thereby to the amount 1° Ab present in the original sample.

A metal nanoparticle, such as Ag, may also be used as a label to indicate the presence of an analyte. In this case, the Ag atoms are oxidized to Ag ions, thereby amplifying the presence of the analyte in proportion to the number of Ag atoms in each nanoparticle.

This process may be embodied in a paper fluidic device, as described herein. In an embodiment, a first channel of a paper fluidic device is infused with 2° Ab/GOx. The first channel is coupled to the sample reservoir, which receives the sample being tested. The sample is added to the sample reservoir and is transported through the first channel where antibodies in the sample can react with the 2° Ab/GOx which is infused in the paper of the first channel. After passing through the first channel, the sample is conducted to a second channel (or a latter portion of the first channel) which is infused with supported antigen particles. As discussed above, the antibodies present in the sample interact with the antigen and become bound to the support. The sample fluid continues to pass through the channel, leaving the support bound antibodies behind. The sample fluid is collected in a final receiving reservoir and is tested for unbound 2° Ab/GOx, as described above. The receiving reservoir may include a predetermined amount of glucose, which will react with any unbound 2° Ab/GOx. Testing for unbound 2° Ab/GOx can be done in the paper microfluidic device when a redox couple is used, as discussed above in the embodiment shown in FIG. 7.

In an alternate embodiment, the sample collected in the receiving reservoir may be transferred to a commercial glucose test strip after the sample fluid has reacted with the preloaded glucose. In an embodiment, a movable strip may be coupled to the support layer. Fluid passes through one or more channels of the support layer onto the movable strip during use. For example, a test strip may be placed in the paper fluidic device, coupled to the reservoir, such that the test strip absorbs the sample after it has reacted with glucose. Alternatively, the test strip may include the receiving reservoir with a predetermined amount of glucose. The strip may receive fluid after the fluid is reacted with glucose. The strip may slide out of the paper fluidic device and be inserted into a personal glucose monitor to determine the amount of glucose present.

Figure 15:
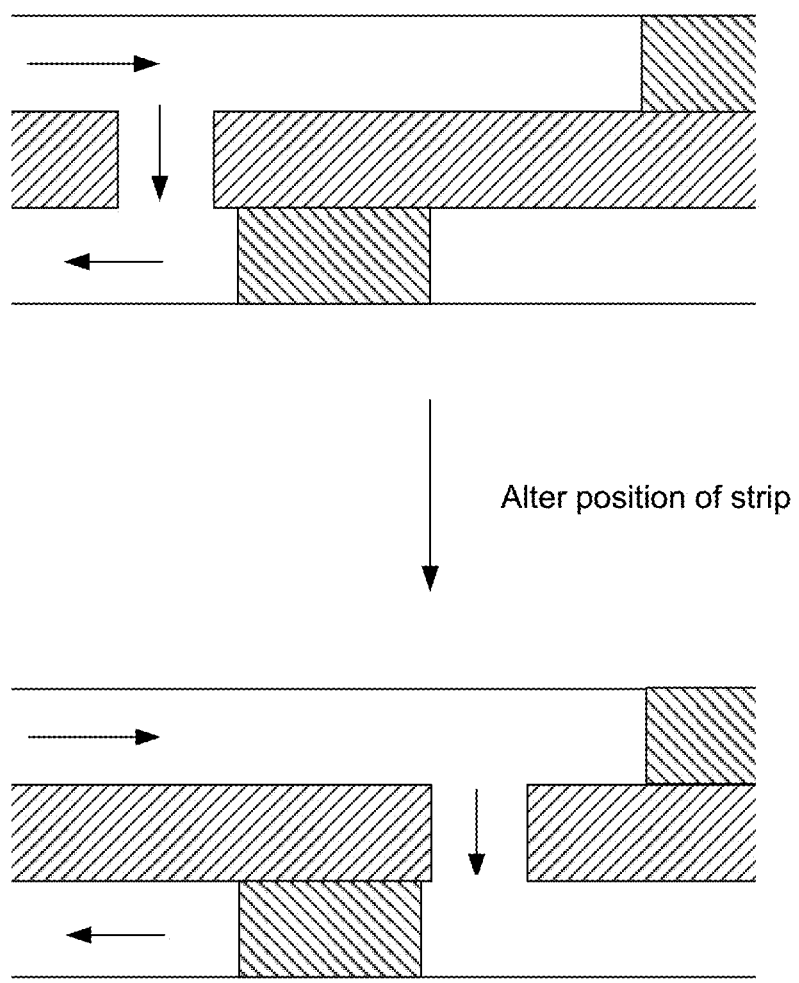
FIG. 15 depicts a cross-sectional side view of a support layer having a movable strip.

In some embodiments, a movable strip may act as a multi-position valve. In FIG. 15, a first support layer (e.g., the top layer in FIG. 15) is composed of a material capable of transporting a liquid using capillary action. The first support layer includes a plurality of channel walls formed on the first support layer. The channel walls define one or more channels and/or one or more reservoirs on the support layer. A second support layer (e.g., the bottom layer in FIG. 15) is composed of a material capable of transporting a liquid using capillary action. The second support layer comprises a plurality of channel walls formed on the second support layer. The channel walls of the second support layer define one or more channels and/or one or more reservoirs on the support layer. A movable layer (e.g., the middle layer of FIG. 15) is positioned between the first support layer and the second support layer. The movable layer includes one or more openings that are alignable with one or more channels or reservoirs of the first support member and one or more channels or reservoirs the second support member. The movable layer is positionable such that fluid added to the first support members passes through the movable layer to the second support member when the one or more openings of the movable layer are aligned with one or more channels or reservoirs of the first support member and one or more channels or reservoirs the second support member. The movable layer is postionable in a first position which allows fluid to pass through the movable layer from the first support layer into a first portion of the second support layer. The movable layer may be subsequently moved into a second position, which alters the flow of fluid from the first support layer into a second portion of the second support layer.

In an embodiment of the process, a paper fluidic device detects a primary antibody in a fluid sample by means of a colorimetric readout, or a potential difference, or an electric current, or a electrical resistance, or a capacitance, or a glucose signal. Said paper fluidic device is designed in such a way that all the necessary reaction elements are disposed in the paper and placed in different locations or different layers and will only come into direct contact with each other upon addition of fluid sample to the inlet of the device, whereby the fluid moves along channels in the paper primarily by capillary action. Said paper fluidic devices, in one embodiment, are constructed from a single piece of paper, which is folded into the final configuration. This approach greatly simplifies device fabrication.

In an embodiment, the first layer of the paper fluidic device may have two or more different solution inlets in order to address both the control and sample assays individually. A sample, for example blood, saliva, urine, or other body fluid, may be dried on an inlet on said first layer, and then buffer solution may be added to the sample and control inlets to initiate flow and activate the system. When a sample is introduced to inlet reservoirs in the first layer, it may move by capillary action into a second layer. The second layer may comprise a filter, for example filter paper, to removes particulates larger than a chosen size. The sample may move by capillary action into a third layer where further separations may take place. For example, if the sample is whole blood, serum may be separated from whole blood by agglomeration of red blood cells, and blood glucose may be removed from the sample by exposing it to immobilized microbeads functionalized with glucose oxidase (GOx) and catalase. GOx will decompose glucose into hydrogen peroxide ($H_2O_2$) and gluconolactone and, later, catalase will decompose the $H_2O_2$ produced into $O_2$ and water. Therefore, glucose-free blood serum will proceed through the paper fluidic device from that point, thereby eliminating contamination of the assay chemistry by the subject's own blood glucose. Additional separations or sample preparation or cleanup steps as are known in the art can be incorporated into a paper fluidic device of the invention. Each operation can be performed sequentially by arranging the steps on subsequent layers of the device.

After the sample has passed through the cleanup steps described above, it may flow by capillary action to a next layer, which may comprise immobile beads functionalized with supported antigen, for example tetanus toxoid. The steps described above and shown in FIG. 13 may take place on this and subsequent layers in order to convert the presence of a primary antibody in the sample to an amount or concentration of 2° Ab/GOx. Subsequent layers of the paper fluidic device may then provide a readout based on the action of GOx as described above.

At least one of the paper layers in the device can be made movable relative to other layers. In this case, the connection and disconnection between channels in adjacent layers can be controlled by changing the position of the movable layer. As shown in FIGS. 16A-16B, a Slip paper analytical device (SlipPAD) comprises at least two paper fluidic layers, on which are patterned hydrophobic and hydrophilic areas, and are fixed on a flat substrate. The paper layers are in close contact so that the hydrophobic pattern (for example, wax) prevents the leaking of liquid. When the position of one layer is changed relative to another, the channels or reservoirs on this layer may align with channels or reservoirs on other layers to form a connection of fluid. Other channels or reservoirs may be fluidly disconnected in a similar way. The SlipPAD can be used for chemical sensing such as immunoassay, nucleic acid-based detection which requires multiple steps (e.g. incubation, rinse, amplification), and can also be used for high-throughput sensing which requires simultaneous manipulating multiple fluids.

Figure 16:
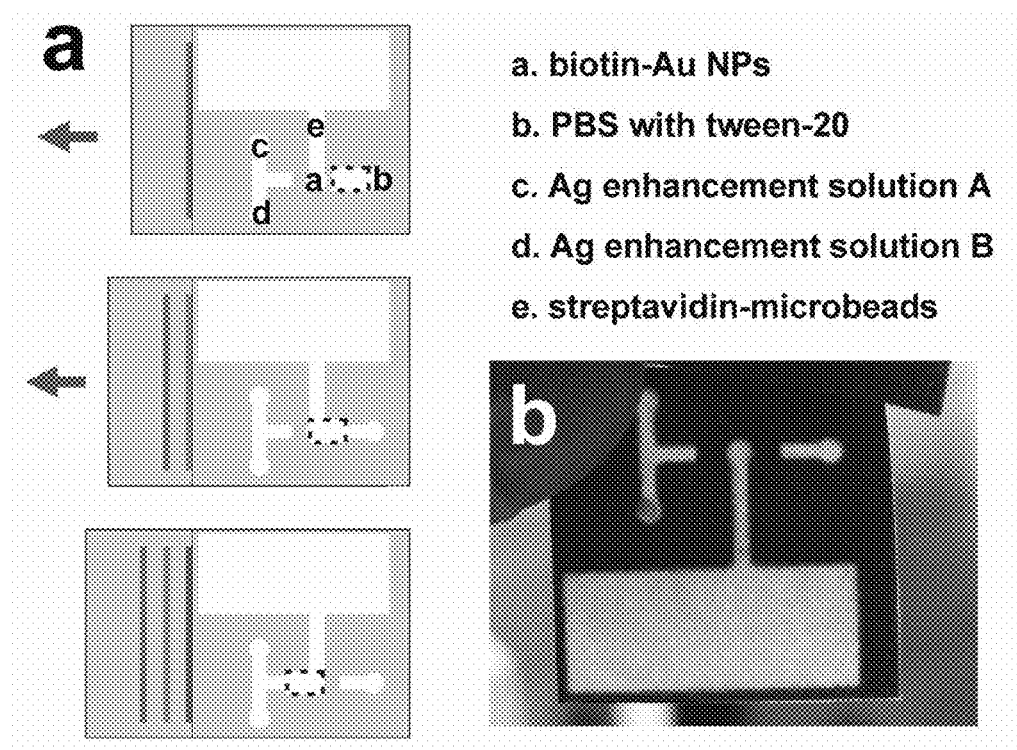
FIGS. 16A-16B depicts an embodiment of a SlipPAD fluidic analytical device that detects metal nanoparticles.

As shown in FIG. 16, a fluidic analytical device includes a first support layer composed of a material capable of transporting a liquid using capillary action. The first support layer includes a plurality of channel walls formed on the first support layer, the channel walls defining one or more channels and/or one or more reservoirs on the support layer. The device also includes a second support layer composed of a material capable of transporting a liquid using capillary action. Similar to the first support layer, the second support layer includes a plurality of channel walls formed on the first support layer, the channel walls defining one or more channels and/or one or more reservoirs on the support layer. The first support layer is coupled to the second support layer such that one or more channels and/or one or more reservoirs of the first support layer are alignable with one or more channels and/or one or more reservoirs of the second support member by moving the first support member with respect to the second support member.

Figure 17:
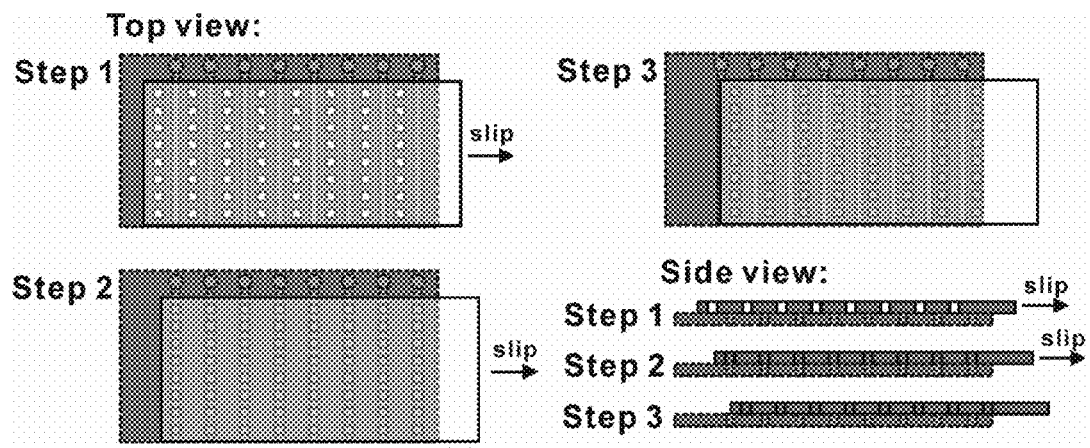
FIG. 17 depicts a schematic diagram of a multiplexed SlipPAD device.

An embodiment of a paper analytical device (PAD), based on the SlipChip concept, is described below. This "SlipPAD" enables robust, high-throughput, multiplexed sensing while maintaining the extreme simplicity of paper-based analysis. The basic operation of an embodiment of a SlipPAD is illustrated in FIG. 17. The device is comprised of two paper fluidic layers which are patterned using wax printing onto chromatographic paper. The two paper layers are attached to rigid substrates, and they are in sufficiently close contact that the wax prevents leakage of liquids between channels and reservoirs, while simultaneously reducing friction between the layers to ensure smooth sliding operation. When the top layer is slipped, fluidic contacts are opened or closed between the two layers. In analogy to previously reported glass SlipChips, this provides a means to simultaneously load large arrays of reaction chambers with precise aliquots of samples and reagents, time reactions, and introduce washing steps to assays. All of these functions are highly developed for plastic and glass chips, but they still represent major hurdles for PAD-based assays. Moreover, this device enables high-throughput chemical sensing, on-chip calibration, and introduction of both preloaded and user-loaded reagents. Hence, it represents a significant advance compared to the present state of the art in the field of paper fluidics.

The SlipPAD has many advantages over prior analytical devices. The SlipPAD has the form factor of a business card, and it enables simultaneous delivery of solution into 285 reservoirs having volumes of ~180 nL with no observable cross contamination. Additionally, fabrication is fast and inexpensive: just a US$600 wax printer and a hot plate are required. In the lab a single individual can produce ~200 devices per hour at a cost of <US$1 each, and these values would likely dramatically increase and decrease, respectively, at production scale. Furthermore, as we show here, the large number of reservoirs on the SlipPAD provide a means for on-chip calibration and multiple, simultaneous replicate assays for improved diagnostic reliability. Finally, the device is naturally amenable to both colorimetric and fluorescent assays.

EXAMPLES

All DNA was ordered from Integrated DNA Technologies, Inc. Streptavidin-labeled glucose oxidase (sGOx) was purchased from Rockland Immunochemicals, Inc. (Gilbertsville, Pa.). Streptavidin-coated polystyrene microbeads and fluorescent polystyrene microbeads with Nile red inside were purchased from Spherotech, Inc. (Lake Forest, Ill.). Adenosine and Glucose oxidase (GOx) from *Aspergillus niger* were obtained from Sigma Aldrich. D-glucose and K3Fe(CN)6 was purchased from Fisher Scientific. All solutions were prepared with deionized water (18.0 MΩ·cm, Milli-Q Gradient System, Millipore). Conductive carbon ink (Creative Materials, Inc. Tyngsboro, Mass.) was used to fabricate electrodes using a coating kit (RD Specialties, Inc. Webster, N.Y.). All paper fluidic devices were fabricated using Grade 1 Whatman chromatographic paper. Scotch thermal laminating pouches (TP5851-20) and a Jorestech impulse thermal edge sealer were used for thermal lamination of the device. A 2.2 µF electrolytic capacitor, a switch, and a breadboard with jumper wires were obtained from RadioShack. All reagents and materials were used as received. The patterning of paper is based on a slight modification of a wax printing procedure reported previously (Carrilho, E. et al. Anal. Chem. 2009, 81, 7091-7095). Briefly, a Xerox 8570DN inkjet printer was used to print wax-based solid ink on Whatman chromatography paper. The paper was then placed on a hot plate with the wax side up for 15 s at 120° C., and then cooled to 20° C. For fabricating electrodes, the patterned paper was placed on a flat glass surface, and then covered with a homemade stencil. An aliquot of carbon ink was dropcast on the stencil. A coating rod was used to coat the carbon ink uniformly onto the patterned paper through the stencil. To cure the carbon ink, the stencil was removed from the paper, and the paper was placed in an oven at 80° C. for 30 min.

For preparing GOx-labeled DNA, 12.5 µM biotin-modified DNA (bDNA) solution was mixed with a 100 µM streptavidin-labeled GOx (sGOx) solution to yield a solution containing 1:1 bDNA and sGOx. The sGOx solution also contains 10 mg/mL bovine serum albumin (BSA) as a stabilizer and 0.1 mg/mL sodium azide as a preservative. After reaction for 24 h, an Amicon 50 K centrifugal filter (Millipore) was used to separate the GOx-labeled bDNA from free bDNA by centrifugal filtering. All solutions were diluted to the same volume for UV-vis characterization, which leads to a concentration of 0.46 μM for both bDNA and sGOx solutions. The UV-vis spectra were taken using a UV-vis spectrometer (Hewlett-Packard 8453).

The characteristic maximum absorptions of protein and DNA are at 280 nm and 260 nm respectively. Note that the absorption of sGOx at 280 nm is significantly higher than that of bDNA at 260 nm at the same concentration due to the difference in extinction coefficients and excess BSA in the sGOx solution. For a solution containing both sGOx and bDNA at a 1:1 molar ratio, the absorption at 260 nm was higher than that of the solution containing only sGOx due to the presence of bDNA in the solution. After filtration using a 50K cut-off centrifugal filter, all the sGOx-labeled bDNA was maintained in the retentate, but the free bDNA passed the filter into the filtrate. The absorption of the retentate at 260 nm was obviously higher than that of the solution containing only sGOx, which demonstrates the formation of the bDNA-sGOx conjugate that was left in the retentate. The absorption of the retentate overlapped with the absorption of the 1:1 sGOx and bDNA mixture, which demonstrates that the ratio of sGOx to bDNA in the final product was approximately 1:1. This agrees with the fact that the absorption of the filtrate at 260 nm was very small. Therefore, almost all bDNA binds to sGOx with minimal free bDNA in the filtrate.

To prepare the device for electrochemical sensing, 12 μL of 100 mM glucose and 100 mM $Fe(CN)_6^{3-}$ in 0.01 M PBS buffer (pH 6.0) was loaded into both halves of the electrochemical cell, and dried in air. A 20 μL solution containing 25 μM biotin-DNA strand was mixed with 20 μL 0.5% (w/v) streptavidin-labeled microbeads. After reaction in the dark for 24 h, the resulting solution was mixed with a 40 μL solution containing 8.4 μM GOx-DNA strand and 12 μM aptamer strand. The solution was dropcast in the split channel on the unfolded device, washed with 0.01 M PBS buffer (pH 7.4) containing 0.1% BSA, and dried in air.

To assemble the origami paper analytical devices (oPADs), the paper was folded by hand. The folded paper device was placed in a thermal laminating pouch, and the pouch was sealed at the edge of the paper device using the impulse thermal edge sealer. Three holes were punched on one side of the pouch. One of the holes was used as inlet and the other two were used to accommodate ohmic contact of the carbon electrodes to two copper wires using Ag adhesive. Five-minute epoxy was used to reinforce the contact.

To use the device for electrochemical sensing, a 20 μL sample aliquot was loaded at the inlet of the oPAD. After 10 min, when the sample fills the whole channel, the oPAD was put on a breadboard. The current generated from it was measured by a Sinometer VA18B digital multimeter (DMM), and simultaneously the charge was accumulated on the capacitor. After 60 s, the switch was closed so that the capacitor discharges toward the DMM instantaneously. The magnitude of the maximum discharge current from the capacitor was recorded. The rate at which DMM measures current depends on conversion rate of analog-to-digital converter, which is usually in the range of 1-100 $s^{-1}$. Although there is no way to measure the conversion rate, the time interval between two current measurements for the DMM used in these studies is about 0.1 s based on video analysis. This means the conversion rate should be >10 $s^{-1}$.

Fluorescence measurements on the paper fluidic devices were made using a Typhoon Trio fluorescence imager (GE Healthcare, Piscataway, N.J.). To quantify these results, the images were imported into Adobe Photoshop CS2 and transferred to gray-scale mode. The mean fluorescence intensity was determined from the image histogram for each detection reservoir, and then it was background-corrected by subtracting the average intensity measured at the center of the paper where no adenosine was present.

For the detection of Au nanoparticles, a SlipPAD shown in FIGS. 16A, 16B was fabricated. The gray or black area shown on the device is wax and the white area is paper channels through which fluid may flow. Different liquid reagents loaded at spots a, b, c and d were sequentially injected into the main channel by slipping the movable layer to left. The channel on the movable layer is highlighted and indexed using a dashed line. The main channel contained streptavidin-coated microbeads trapped in the paper channel. First, a suspension of (a) biotin-labeled Au nanoparticles was injected, and the nanoparticles were captured by the microbeads through biotin-streptavidin binding. The biotin-Au nanoparticles were obtained from Cytodiagnositcs (CGB5K-40-25) and were about 40 nm in diameter, with a concentration of $3.58 \times 10^{11}$ particles/mL. Next, a washing buffer (b) was injected to wash away any non-specifically adsorbed Au nanoparticles. The washing buffer was 0.01 M phosphate-buffered saline (at pH 7.4) containing 0.05% polysorbate 20 (tween-20). The tween-20 is used as a surfactant to reduce nonspecific adsorption in the paper channel. Finally, silver enhancement solution A and B were injected to stain the captured Au nanoparticles on the microbeads. The Ag enhancement solution A and B were obtained from Sigma (no. S5020 and S5145). When mixed together, they react to produce Ag metal, and this reaction is catalyzed by Au nanoparticles. In this way, the Ag enhancement solutions are used to detect the presence of trace amounts of Au nanoparticles. The result is shown in FIG. 16B. In FIG. 16B, there is a dark spot formed at the location where the streptavidin-labeled microbeads were immobilized in the paper, (indicated by "e" in FIG. 16A). Au nanoparticles were captured on the microbeads by means of the biotin-streptavidin interaction, and the Au nanoparticles catalyzed the Ag enhancement reaction, which lead to the dark spot in the channel.

Figure 18:
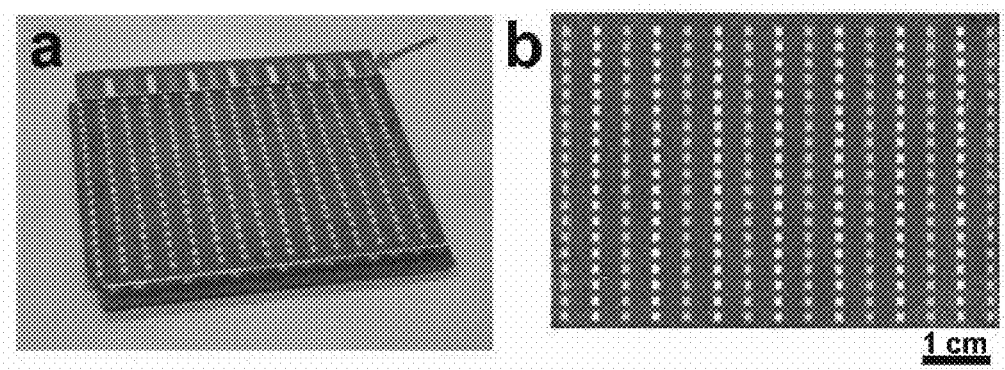
FIGS. 18A-B depicts an embodiment of a multiplexed SlipPAD device.

FIG. 18A is a photograph of a simple two-level SlipPAD. The 285 reservoirs, which have lateral dimensions of 1 mm×1 mm and volumes of ~180 nL, were printed onto Whatman Grade 1 chromatography paper using a Xerox model 8570DN wax printer. The SlipPAD includes two paper fluidic layers patterned by printing black-colored wax. The paper was then placed on a hot plate with the wax side up for 45 s at 120° C. and then cooled to 20° C. For preparing the reagent solution for the colorimetric BSA assay, 30 μL of 4% $CuSO_4$ solution was mixed with 90 μL of bicinchoninic acid solution from the assay kit. For the colorimetric glucose assay and the fluorescent BSA assay, all the reagents are from the assay kits and are prepared according to the instructions of the kit provider. Next, 2.0 μL aliquots of the reagent solutions were dropcast onto the reservoir (~2 mm by 2 mm) patterned on the chromatography paper. The solution was allowed to dry at 20° C. under nitrogen. The paper fluidic layers were then attached to glass slides using the glue stick. 30 μL aliquots of 0.010 M PBS solution (pH 7.4) containing either 1.0 mM erioglaucine (blue) or 1.0 mM tartrazine (yellow) were loaded at the inlets of channels (1.5 mm wide, marked with a red arrow) on the bottom layer.

The top layer is then slipped to the left so that the solutions wick into all of 285 reservoirs in the top layer. Each of the reservoirs was 1 mm square and 180 μm in depth, which is equivalent to a geometric volume of 180 nL. Note that this value is an upper bound and does not take into account the enclosed volume of cellulose. All the reservoirs are filled within 2 s. The top paper layer of the device is then scanned using an office scanner (HP C6180). As shown in FIG. 18B, the colored solutions were delivered to the designated reservoirs without cross contamination.

Figure 19:
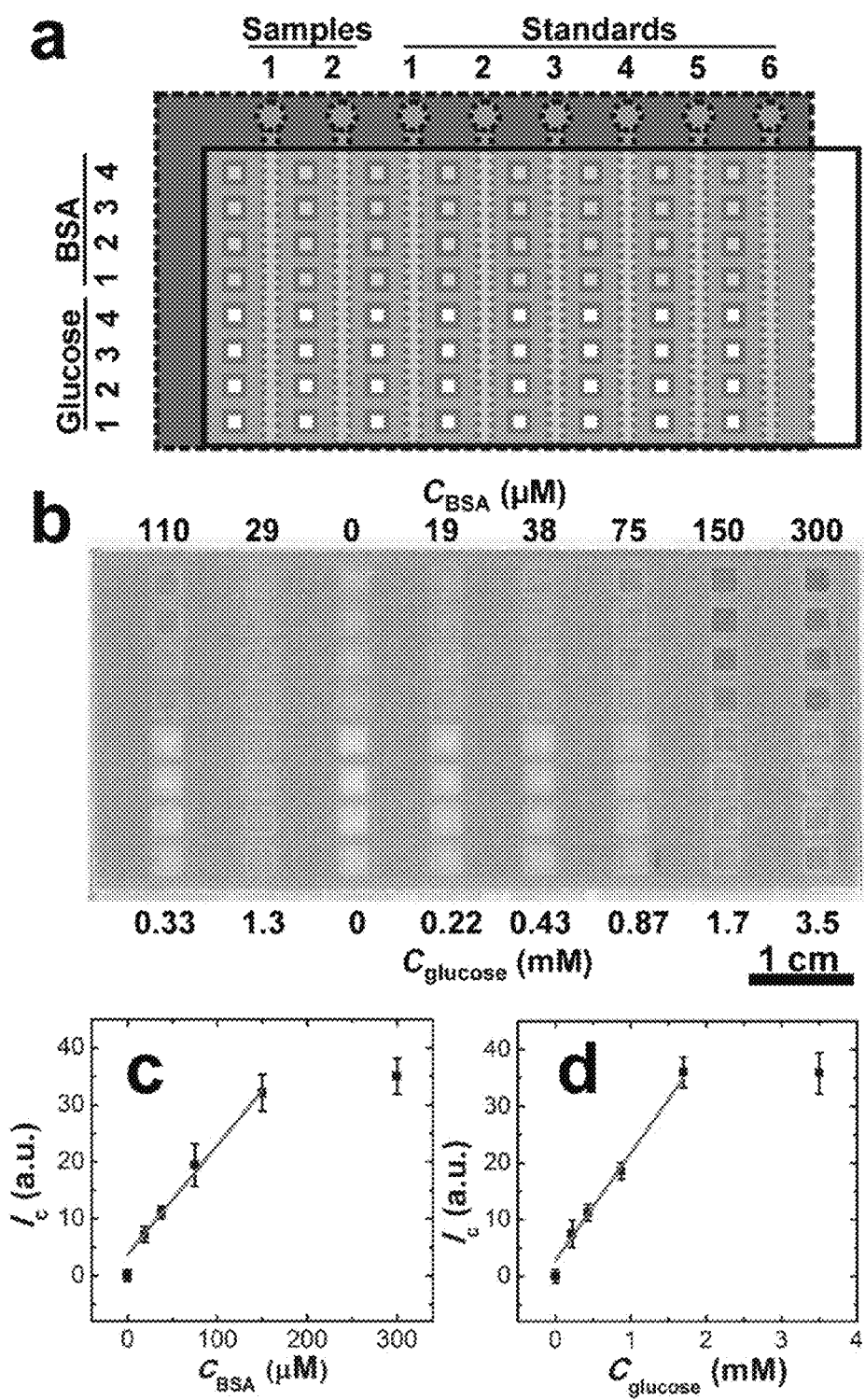
FIGS. 19A-D depict colorimetric data collected from the SlipPAD device.

To demonstrate the applicability of the device for high-throughput multiplexed sensing, a SlipPAD having 64 detection reservoirs was fabricated by wax printing. FIG. 19A depicts a schematic diagram illustrating the design of the SlipPAD for detection of glucose and BSA. The bottom layer and its channels (2.5 mm wide) are outlined using dashed black lines. FIG. 19B shows a scanometric image of the top layer of the SlipPAD showing the detection reservoirs (2 mm square) after completion of the assay. The concentrations of BSA and glucose in each standard or sample are indicated. Cyan-colored wax (rather than black) was used to improve the contrast of the colorimetric assays. Each reservoir in the upper half of the array was preloaded with a dried colorimetric indicator for detection of bovine serum albumin (BSA), and each reservoir in the bottom half was preloaded with a dried indicator for the presence of glucose. The detection of BSA is based on a bicinchoninic acid assay, in which peptide bonds present in BSA reduce $Cu^{2+}$ to $Cu^+$, leading to a purple-colored chelate complex. The detection of glucose is based on a two-step reaction: (1) glucose oxidase-catalyzed oxidation of glucose to yield $H_2O_2$ and (2) horseradish peroxidase-catalyzed oxidation of o-dianisidine by $H_2O_2$ to yield a brown-colored compound.

For both assays, 30 µL aliquots of standard solutions containing BSA and glucose at known concentrations were injected into the six channels on the right (FIG. 19A). Likewise, 30 µL aliquots of samples having intermediate concentrations were injected into the two channels on the left. The top layer was then slipped to the left so that the standards and samples in the channels wicked into the designated reservoirs to react with the preloaded assay reagents. Finally, the top layer was slipped further to the left to fully isolate the top reservoirs from the channels. The colors, which are related to the concentrations of the analytes, were developed within 10 min. A single SlipPAD enables four simultaneous replicate assays for both the standards and the samples.

As shown in FIG. 19B, the intensity of the color change from green to purple is correlated to the BSA concentration, and the intensity of the color change from colorless to brown is correlated to the glucose concentration. Importantly, no cross contamination between the BSA and glucose assays is observed. The color changes of the standard solutions provide a guide for naked-eye, semi-quantification of the concentrations of BSA and glucose in the samples. For example, the purple color in the reservoirs containing Sample 1 (110 µM BSA) is more intense than that of Standard 4 containing 75 µM BSA but less intense than that of Standard 5 containing 150 µM BSA, indicating the concentration of BSA in Sample 1 is between 75 µM and 150 µM. To better quantify these results, the image was imported into Adobe Photoshop CS2, and the color intensity was obtained from a histogram of each reservoir. The color intensities were then linearly correlated to the concentrations of BSA and for glucose using the calibration curves in FIGS. 19C and 19D respectively. The red lines are linear fits from 19 to 150 µM for BSA and from 0.22 to 1.7 mM for glucose. The error bars represent standard deviations for four replicate assays. For both FIG. 19C and FIG. 19D, the color intensities were normalized by subtracting the intensity of the sample containing no BSA or glucose. The limits of detection, defined as 3 times the standard deviation of the sample containing no BSA or glucose divided by the slope of the calibration curve, are 15 µM for BSA and 0.19 mM for glucose. The intensities of the four replicate assays are quite reproducible (relative standard deviation <3%). On the basis of the calibration curves, the concentrations of BSA and glucose in Sample 1 are determined to be 100 µM and 0.30 mM, respectively, and the concentrations of BSA and glucose in Sample 2 are 26 µM and 1.4 mM, respectively. The deviations from the actual concentrations are all <12%.

In the example discussed above, the colorimetric reagents were manually loaded into each reservoir using a pipette. However, for larger arrays or large numbers of SlipPADs, this approach is untenable. To address this problem, the SlipPAD may be configured to be loaded with reagents by an end user. In one embodiment, multiple reservoirs were connected by a channel so that all of them were filled with reagents using a single injection. This example also demonstrates that in addition to colorimetry, the SlipPAD can also be interrogated using fluorescence. The assay is based on the dye epicocconone, which exhibits enhanced fluorescence in the presence of BSA.

Figure 20:
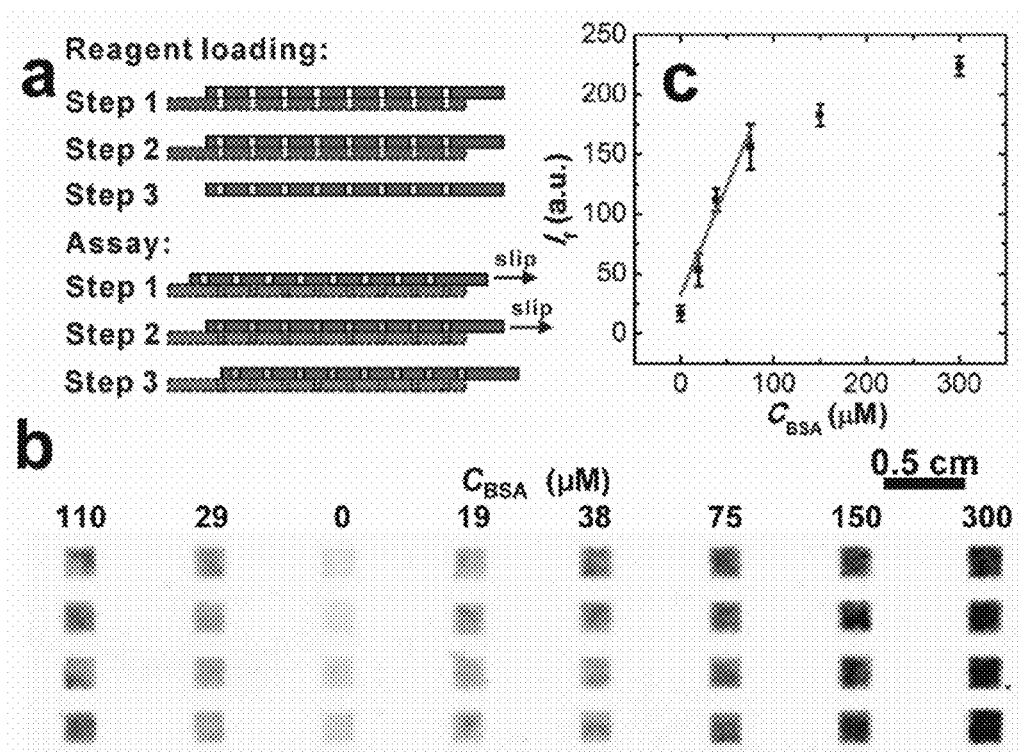
FIG. 20 depicts fluorescence data collected from the SlipPAD device.

As shown in FIG. 20A, 25 µL aliquots of assay reagents were delivered into the reservoirs of the top layer through the channels on the bottom layer. After drying, the top layer was removed and connected to a second bottom layer for injection of sample and standard solutions. Note that switching layers is very easy. Subsequent operations of this Slip-PAD are the same as for the colorimetric assay, except that a fluorescence scanner was used to obtain the images shown in FIG. 20B. The key result is that the fluorescence intensity is linearly correlated to the concentration of BSA from 19 to 75 µM (FIG. 20C) and the detection limit is 10 µM. The concentrations of BSA for the samples were found to be 100 and 31 µM. The deviations from the actual concentrations are within 9%.

A SlipPAD is exemplified here for high-throughput chemical sensing. This method provides some important advantages, compared to previously reported SlipChips or µPADs, for certain low-cost applications. Specifically, a single individual can produce ~200 devices per hour and the cost per device is less than $1. Moreover, the SlipPAD enables parallel delivery of liquid into a large array containing 285 reservoirs within seconds. Finally, the flexible and highly parallel liquid-handling capability can be harnessed for high-throughput quantitative chemical sensing with on-chip calibration and replicate measurements to improve the reliability of diagnostic results. The SlipPAD is a particularly useful format for applications including point-of-care, multiplexed assays under resource-limited conditions.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A fluidic analytical device comprising:
a support layer, wherein the support layer comprises a single sheet of material capable of transporting a liquid using capillary action; and
a plurality of channel walls formed on the support layer, wherein the channel walls define channels on the support layer, wherein a fluid added to the support layer in one or more of the channels is conducted through the channels by capillary action.

2. The fluidic device of claim 1, wherein the support layer comprises paper.

3. The fluidic device of claim 1, wherein the channel walls are formed from a liquid impermeable material.

4. The fluidic device of claim 3, wherein the liquid impermeable material is a photoresist material.

5. The fluidic device of claim 3, wherein the liquid impermeable material is a solid wax material.

6. The fluidic device of claim 1, wherein the channel walls define one or more inlets, one or more reservoirs, and one or more channels that direct a fluid from the inlet to the reservoir.

7. The fluidic device of claim 6, wherein the reservoir comprises a reagent for chemical analysis.

8. The fluidic device of claim 7, wherein the reagent is a reagent for electrochemical analysis.

9. The fluidic device of claim 1, further comprising chemically sensitive material disposed in the support layer in one or more of the channels, wherein the chemically sensitive material is capable of producing a detectable signal when an analyte is present.

10. The fluidic device of claim 9, wherein the chemically sensitive material comprises antibody sensitive particles capable of binding to antibodies in a fluid sample.

11. The fluidic device of claim 1, wherein the fluidic analytical device comprises a first channel and a second channel, wherein the first channel comprises chemically sensitive particles, and wherein the second channel comprises chemically inert particles.

12. The fluidic device of claim 1, further comprising electrodes formed on the support layer using a conductive material.

13. The fluidic device of claim 1, wherein the support layer is encapsulated in a polymeric material.

14. The fluidic device of claim 1, further comprising a movable strip coupled to the support layer, wherein fluid passes through one or more channels of the support layer onto the movable strip during use.

15. The fluidic device of claim 1, further comprising a movable strip coupled to the support layer, wherein the movable strip is positionable within the support to alter the flow of fluids through one or more channels.

16. The fluidic device of claim 15, wherein the movable strip is removable from the fluidic analytical device.

17. The fluidic device of claim 1, further comprising liquid conductive zones that connect one or more layers, inlets, reservoirs, channels coupling the inlets to the reservoirs, vias coupling layers, and water-impermeable barriers that redirect the fluid path into an adjacent conductive zone.

18. The fluidic device of claim 1, wherein the support layer comprises a top layer comprising a plurality of reservoirs and a bottom layer comprising a plurality of reservoirs, wherein the plurality of reservoirs in the top layer are alignable with the plurality of reservoirs of the bottom layer by sliding the top layer over the bottom layer.

19. The fluidic device of claim 1, wherein the plurality of channel walls are positioned relative to one another on the support layer such that folding the support layer crates a three dimensional fluidic device that includes inlets, reservoirs, and channels coupling the inlets to the reservoirs.

* * * * *